US012615965B2

(12) United States Patent
Matsuda et al.

(10) Patent No.: US 12,615,965 B2
(45) Date of Patent: Apr. 28, 2026

(54) PIEZOELECTRIC MATERIAL, PIEZOELECTRIC ELEMENT, AND ELECTRONIC APPARATUS

(71) Applicant: CANON KABUSHIKI KAISHA, Tokyo (JP)

(72) Inventors: Takanori Matsuda, Tokyo (JP); Tatsuo Furuta, Tokyo (JP); Hisato Yabuta, Tokyo (JP); Akira Uebayashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1092 days.

(21) Appl. No.: 17/685,558

(22) Filed: Mar. 3, 2022

(65) Prior Publication Data

US 2022/0293849 A1 Sep. 15, 2022

(30) Foreign Application Priority Data

Mar. 11, 2021 (JP) ................................. 2021-039641

(51) Int. Cl.
*H10N 30/853* (2023.01)
*A61B 8/00* (2006.01)
(Continued)

(52) U.S. Cl.
CPC ......... *H10N 30/853* (2023.02); *A61B 8/4444* (2013.01); *B06B 1/0644* (2013.01); *B41J 2/14201* (2013.01); *H04N 23/811* (2023.01)

(58) Field of Classification Search
CPC .......................... B41J 2/14201; B41J 2/14233; B41J 2202/03; H10N 30/8536; H10N 30/853;
(Continued)

(56) References Cited

U.S. PATENT DOCUMENTS 4,696,810 A     9/1987   Shirasaki et al.
6,660,414 B1 *  12/2003  Xiang .................. C01G 23/006
                                                        106/287.19
(Continued)

FOREIGN PATENT DOCUMENTS

JP        61-53114 A      3/1986
JP      2006-96652 A      4/2006
(Continued)

OTHER PUBLICATIONS

Saburo Nagakura et al. (ed.), Iwanami Physicochemical Dictionary, 5th Edition, p. 1268-1269 (Iwanami Shoten, Publishers; Feb. 20, 1998).
(Continued)

*Primary Examiner* — J. San Martin
(74) *Attorney, Agent, or Firm* — Venable LLP

(57) ABSTRACT

Provided is a piezoelectric material which is free of lead, has small temperature dependence of a piezoelectric constant and has a satisfactory piezoelectric constant. The piezoelectric material includes: an oxide having a perovskite-type structure containing Ba, Ca, Ti, and Zr; Mn; Bi; and W, wherein a ratio of the sum of the Ba and the Ca with respect to the sum of the Ti and the Zr is 0.986 or more and 1.02 or less, and wherein, with respect to 100 parts by mass of the oxide, a content of the Mn is 0.040 part by mass or more and 0.360 part by mass or less, a content of the Bi is 0.050 part by mass or more and 0.240 part by mass or less, and a content of the W is 0.100 part by mass or more and 0.380 part by mass or less.

19 Claims, 18 Drawing Sheets

(51) Int. Cl.

| | | |
|---|---|---|
| *B06B 1/06* | (2006.01) | |
| *B41J 2/14* | (2006.01) | |
| *H04N 23/81* | (2023.01) | |

(58) Field of Classification Search

CPC .... H10N 30/097; H10N 30/50; H10N 30/706; H10N 30/074; H10N 30/2047; H04N 23/811; B06B 1/0644; A61B 8/4444; H02N 2/163

See application file for complete search history.

(56) References Cited

U.S. PATENT DOCUMENTS

| | | | |
|---|---|---|---|
| 9,144,971 | B2 | 9/2015 | Watanabe et al. |
| 9,166,140 | B2 | 10/2015 | Tanaka et al. |
| 9,231,188 | B2 | 1/2016 | Suzuki et al. |
| 9,306,150 | B2 | 4/2016 | Tanaka et al. |
| 9,412,931 | B2 | 8/2016 | Shimada et al. |
| 9,614,141 | B2 * | 4/2017 | Shimizu ................. H10N 30/20 |
| 9,722,170 | B2 | 8/2017 | Watanabe et al. |
| 9,893,268 | B2 | 2/2018 | Matsuda et al. |
| 9,917,245 | B2 | 3/2018 | Kubota et al. |
| 10,727,395 | B2 | 7/2020 | Yabuta et al. |
| 10,868,232 | B2 | 12/2020 | Saito et al. |
| 2007/0202036 | A1 | 8/2007 | Jongen et al. |
| 2008/0145292 | A1 | 6/2008 | Shirakawa et al. |
| 2008/0302658 | A1 * | 12/2008 | Sasaki ................ H10N 30/8554 252/62.9 R |
| 2017/0101345 | A1 | 4/2017 | Shimada et al. |
| 2021/0328131 | A1 | 10/2021 | Furuta et al. |

FOREIGN PATENT DOCUMENTS

| | | |
|---|---|---|
| JP | 2007-269542 A | 10/2007 |
| JP | 2013-123150 A | 6/2013 |
| JP | 2015-34118 A | 2/2015 |
| JP | 2015-034121 A | 2/2015 |

OTHER PUBLICATIONS

Yasuo Hikichi et al,"Preparation and Dielectric Properties of WO3-Doped Small-Grained BaTiO3 Ceramics," 24 Jpn. J. Appl. Phys. 1039-1041 (1985).

Notice of Reasons for Refusal in Japanese Application No. 2021-039641 (Aug. 2024).

* cited by examiner

DUST REMOVING DEVICE
310

320 DIAPHRAGM

333
SECOND
ELECTRODE

332
FIRST
ELECTRODE

331 PIEZOELECTRIC
MATERIAL

330
PIEZOELECTRIC
ELEMENT

310

330

320

332

(a)                    (b)                    (c)

PIEZOELECTRIC MATERIAL, PIEZOELECTRIC ELEMENT, AND ELECTRONIC APPARATUS

BACKGROUND OF THE INVENTION

Field of the Invention

The present invention relates to a piezoelectric material, and more particularly, to a piezoelectric material free of lead. The present invention also relates to a piezoelectric material, a piezoelectric element, a multilayered piezoelectric element, a liquid discharge head, a liquid discharge device, an ultrasonic motor, an optical apparatus, a vibration device, a dust removing device, an image pickup apparatus, a piezoelectric acoustic component, an electronic apparatus, an ultrasonic probe, and an ultrasonic diagnostic system each using the piezoelectric material.

Description of the Related Art

Lead zirconate titanate containing lead is a typical piezoelectric material, and is used in a variety of piezoelectric devices, such as an actuator, an oscillator, a sensor, and a filter. However, a lead content in a discarded piezoelectric material may elute into soil to adversely affect an ecosystem. Accordingly, in order to exclude lead from piezoelectric devices, research and development on lead-free piezoelectric materials are actively conducted.

When a piezoelectric element is used in a product such as a household electrical appliance or used for medical diagnosis applications, it is required that the piezoelectric performance not be greatly fluctuated within an operating temperature range of the product. When parameters related to the piezoelectric performance, for example, an electromechanical coupling coefficient and a piezoelectric constant, are greatly fluctuated (for example, by 30% or more) depending on the temperature, it becomes difficult to obtain stable element performance within the operating temperature range. When a piezoelectric material undergoes phase transition, the piezoelectricity becomes maximum at the phase transition temperature. Accordingly, the phase transition is the largest factor for fluctuating the piezoelectric characteristics. Thus, when changes in piezoelectric performance within the operating temperature range of the product need to be reduced, a piezoelectric material that does not have a phase transition temperature within the operating temperature range is required.

In Japanese Patent Application Laid-Open No. 2015-034121, there is disclosed a piezoelectric material characterized by including: a main component containing a perovskite-type metal oxide represented by the following general formula (1); a first sub-component formed of Mn; a second sub-component formed of Li; and a third sub-component formed of Bi, wherein a content of the Mn is 0.04 part by mass or more and 0.36 part by mass or less in terms of a metal with respect to 100 parts by mass of the metal oxide, a content "α" of the Li is 0.0012 part by mass or less (including 0 parts by mass) in terms of a metal with respect to 100 parts by mass of the metal oxide, and a content "β" of the Bi is 0.042 part by mass or more and 0.850 part by mass or less in terms of a metal with respect to 100 parts by mass of the metal oxide:

$$(Ba_{1-x}C_x)_a(T_{1-y-z}Zr_ySn_z))_3 \qquad (1)$$

where "x", "y", "z", and "a" satisfy $0.09 \leq x \leq 0.30$, $0.025 \leq y \leq 0.085$, $0 \leq z \leq 0.02$, and $0.986 \leq a \leq 1.02$, respectively.

The invention as described in Japanese Patent Application Laid-Open No. 2015-034121 provides a piezoelectric material in which the piezoelectric characteristics within the operating temperature range are less fluctuated and which has a high mechanical quality factor and satisfactory piezoelectric characteristics. However, the piezoelectric constant thereof is not large and cannot be said to be sufficient. In particular, a temperature difference between a phase transition point $T_{to}$ between a tetragonal crystal and an orthorhombic crystal and a Curie temperature $T_C$, which is a phase transition point between the tetragonal crystal and a cubic crystal, in a low-temperature region (in the vicinity of $-30°$ C.) is about $140°$ C., and hence a minimum point of the piezoelectric constant falls within a high-temperature region (in the vicinity of $50°$ C.) within the operating temperature range.

Because of the foregoing, there is a problem in that sufficient performance cannot be exhibited particularly in a device that is generally used in the vicinity of $50°$ C.

In the related art, there are problems in that the piezoelectric performance of a lead-free piezoelectric ceramics is greatly fluctuated within the operating temperature range of a piezoelectric element, and further the piezoelectric constant thereof is small.

The present invention has been made to solve the above-mentioned problems, and provides a piezoelectric material which is free of lead, has small temperature dependence of a piezoelectric constant within an operating temperature range, and has a satisfactory piezoelectric constant. The present invention also provides a piezoelectric material, a piezoelectric element, a multilayered piezoelectric element, a liquid discharge head, a liquid discharge device, an ultrasonic motor, an optical apparatus, a vibration device, a dust removing device, an image pickup apparatus, a piezoelectric acoustic component, an electronic apparatus, an ultrasonic probe, and an ultrasonic diagnostic system each using the piezoelectric material.

SUMMARY OF THE INVENTION

A piezoelectric material of the present invention for solving the above-mentioned problems is characterized by including: an oxide having a perovskite-type structure containing Ba, Ca, Ti, and Zr; Mn; Bi; and W, wherein "x", which represents a molar ratio of the Ca with respect to a sum of the Ba and the Ca, satisfies $0.085 \leq x \leq 0.150$, wherein "y", which represents a molar ratio of the Zr with respect to a sum of the Ti and the Zr, satisfies $0.025 \leq y \leq 0.085$, wherein a ratio of the sum of the Ba and the Ca with respect to the sum of the Ti and the Zr is 0.986 or more and 1.02 or less, and wherein, in terms of a metal with respect to 100 parts by mass of the oxide, a content of the Mn is 0.040 part by mass or more and 0.360 part by mass or less, a content of the Bi is 0.050 part by mass or more and 0.240 part by mass or less, and a content of the W is 0.100 part by mass or more and 0.380 part by mass or less.

The piezoelectric material of the present invention is characterized by being polarized.

The piezoelectric material of the present invention is characterized by having an average equivalent circle diameter of a crystal of 2.0 μm or more and 12.0 μm or less.

The piezoelectric material of the present invention is characterized in that the oxide is represented by the following general formula (1):

$$(Ba_{1-x}Ca_x)_a(Ti_{1-y}Zr_y)O_3 \tag{1}$$

where "x", "y", and "a" satisfy $0.085 \le x \le 0.150$, $0.025 \le y \le 0.085$, and $0.986 \le a \le 1.02$, respectively.

The piezoelectric material of the present invention is characterized by having a dielectric loss tangent at a frequency of 1 kHz of 0.010 or less.

A piezoelectric material of the present invention is characterized by including the above-mentioned piezoelectric material.

A piezoelectric element of the present invention is characterized by including at least: an electrode; and a piezoelectric material portion, wherein the piezoelectric material portion contains the above-mentioned piezoelectric material.

A multilayered piezoelectric element of the present invention is characterized in that the electrode and the piezoelectric material portion are stacked alternately, the electrode contains Ag and Pd, and a mass ratio M1/M2 between a content mass M1 of the Ag and a content mass M2 of the Pd is $0.25 \le M1/M2 \le 4.0$.

In addition, the piezoelectric element of the present invention is characterized in that the electrode contains at least any one kind selected from the group consisting of: Ni; and Cu.

A liquid discharge head of the present invention is characterized by including at least: a liquid chamber including a vibration unit including the above-mentioned piezoelectric element or the above-mentioned multilayered piezoelectric element; and a discharge port communicating to the liquid chamber.

A liquid discharge device of the present invention is characterized by including: a transfer material-carrying unit; and the above-mentioned liquid discharge head.

A vibration actuator of the present invention is characterized by including: a vibrating body including the above-mentioned piezoelectric element or the above-mentioned multilayered piezoelectric element; and a contact body to be brought into contact with the vibrating body.

An optical apparatus of the present invention is characterized by including a drive unit including the above-mentioned vibration actuator.

A vibration device of the present invention is characterized by including a vibrating body including a diaphragm including the above-mentioned piezoelectric element or the above-mentioned multilayered piezoelectric element.

A dust removing device of the present invention is characterized by including a vibration unit including the above-mentioned vibration device.

An image pickup apparatus of the present invention is characterized by including at least: the above-mentioned dust removing device; and an image pickup element unit, wherein the diaphragm of the dust removing device is arranged on a light receiving plane side of the image pickup element unit.

An ultrasonic probe of the present invention is characterized by including a transducer including the above-mentioned piezoelectric element.

An ultrasonic diagnostic system of the present invention is characterized by including: the above-mentioned ultrasonic probe; and a receiving unit configured to receive a signal output from the ultrasonic probe.

An electronic apparatus of the present invention is characterized by including a piezoelectric acoustic component including the above-mentioned piezoelectric element or the above-mentioned multilayered piezoelectric element.

Further features of the present invention will become apparent from the following description of exemplary embodiments with reference to the attached drawings.

DESCRIPTION OF THE EMBODIMENTS

Figure 1:
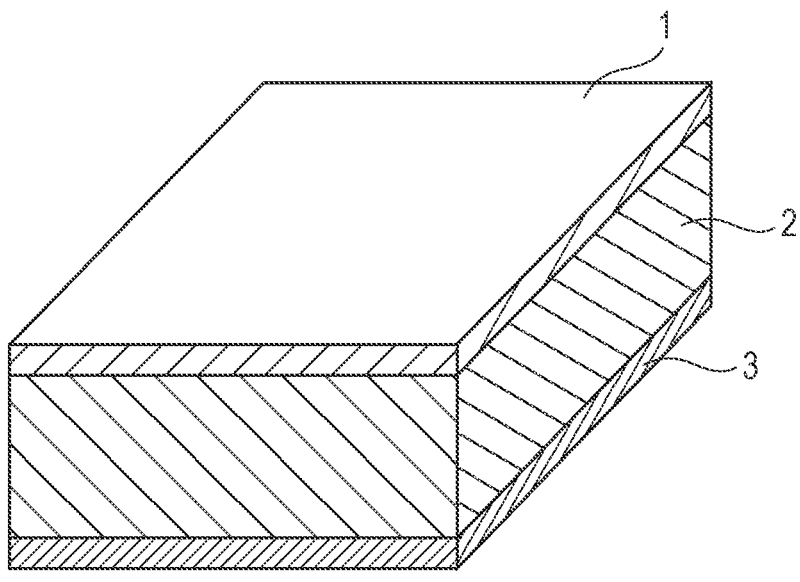
FIG. 1 is a schematic view for illustrating the configuration of a piezoelectric element according to one embodiment of the present invention.

Now, embodiments of the present invention are described.

The present invention provides a lead-free piezoelectric material which contains (Ba, Ca)(Ti, Zr)O$_3$ as a main component, has small temperature dependence of a piezoelectric constant within an operating temperature range of, for example, from 0° C. to 60° C., and has satisfactory piezoelectricity. The piezoelectric material of the present invention may be utilized for various applications, such as a memory and a sensor, through utilization of the characteristics as a ferroelectric.

The piezoelectric material of the present invention includes: an oxide having a perovskite-type structure containing Ba, Ca, Ti, and Zr; Mn; Bi; and W, wherein "x", which represents a molar ratio of the Ca with respect to a sum of the Ba and the Ca, satisfies $0.085 \leq x \leq 0.150$, wherein "y", which represents a molar ratio of the Zr with respect to a sum of the Ti and the Zr, satisfies $0.025 \leq y \leq 0.085$, wherein a ratio of the sum of the Ba and the Ca with respect to the sum of the Ti and the Zr is 0.986 or more and 1.02 or less, and wherein, in terms of a metal with respect to 100 parts by mass of the oxide, a content of the Mn is 0.040 part by mass or more and 0.360 part by mass or less, a content of the Bi is 0.050 part by mass or more and 0.240 part by mass or less, and a content of the W is 0.100 part by mass or more and 0.380 part by mass or less.

The piezoelectric material of the present invention may be represented by the following general formula (1):

$$(Ba_{1-x}Ca_x)_a(Ti_{1-y}Zr_y)O_3 \qquad (1)$$

where "x", "y", and "a" satisfy $0.085 \leq x \leq 0.150$, $0.025 \leq y \leq 0.085$, and $0.986 \leq a \leq 1.02$, respectively.

In the present invention, a perovskite-type metal oxide refers to a metal oxide having a perovskite-type structure (sometimes referred to as perovskite structure) as described in the 5th edition of the Iwanami Physical and Chemical Dictionary (Iwanami Shoten, Publishers, published on Feb. 20, 1998). A metal oxide having a perovskite-type structure is generally represented by the chemical formula of ABO$_3$. In the perovskite-type metal oxide, the elements A and B occupy specific positions in a unit cell called an A site and a B site, respectively, in the form of ions. For example, in the case of a cubic unit cell, the element A is located at an apex of a cube, and the element B is located at a body center. The element O occupies a face-centered position of the cube as an anion of oxygen.

Herein, the content of each of sub-components, such as Mn, Bi, and W, "in terms of a metal" indicates the following. W is taken as an example. The contents of the respective metals of Ba, Ca, Ti, Zr, Mn, Bi, and W are measured from the piezoelectric material by X-ray fluorescence analysis (XRF), inductively coupled plasma (ICP) emission spectrometry, atomic absorption spectroscopy, or the like. From the contents, elements forming a metal oxide represented by the general formula (1) are converted into oxides, and the total mass thereof is defined as 100. The content of W indicates a value obtained as a ratio of the mass of W with respect to the total mass.

The piezoelectric material of the present invention contains a perovskite-type metal oxide as a primary phase from the viewpoint of an insulating property. Whether or not the perovskite-type metal oxide is a primary phase is determined by, for example, whether the maximum diffraction intensity derived from the perovskite-type metal oxide is 100 times or more as large as the maximum diffraction intensity derived from an impurity phase in X-ray diffraction. It is preferred that the piezoelectric material be formed of only the perovskite-type metal oxide because the insulating property becomes highest. The "primary phase" refers to a case in which, when the powder X-ray diffraction of the piezoelectric material is performed, the strongest diffraction intensity peak is ascribed to the perovskite-type structure. It is more preferred that the piezoelectric material contain a perovskite-type metal oxide as a "single phase" in which crystals each having a perovskite-type structure occupy substantially the entire piezoelectric material.

The metal oxide represented by the general formula (1) means that the metal elements located at the A site are Ba and Ca, and the metal elements located at the B site are Ti and Zr. However, part of Ba and Ca may be located at the B site. Similarly, part of Ti and Zr may be located at the A site.

The molar ratio of the B site elements to the 0 element in the general formula (1) is 1:3, but a case in which the ratio of element amounts slightly deviates therefrom (for example, from 1.00:2.94 to 1.00:3.06) is also encompassed in the scope of the present invention as long as the metal oxide has a perovskite-type structure as a primary phase.

The form of the piezoelectric material according to the present invention is not limited. Any one of the forms of a ceramics, powder, a monocrystal, a film, a slurry, and the like may be used, and it is preferred that the piezoelectric material have a ceramics form. The "ceramics" as used herein refers to an aggregate (also referred to as "bulk body") of crystal grains, a so-called polycrystal, which contains a metal oxide as a basic component and is baked by heat treatment. The ceramics also encompasses ones processed after sintering.

When the piezoelectric material of the present invention contains an oxide having a perovskite-type structure in which the range of the Ca amount "x" is $0.085 \leq x \leq 0.150$ and the range of the Zr amount "y" is $0.025 \leq y \leq 0.085$, and the Mn amount is 0.040 part by mass or more and 0.360 part by mass or less, the Bi amount is 0.050 part by mass or more and 0.240 part by mass or less, and the W amount is 0.100 part by mass or more and 0.380 part by mass or less with respect to 100 parts by mass of the oxide, a satisfactory piezoelectric constant can be obtained within an operating temperature range.

The range of the Ca amount "x" is $0.085 \leq x \leq 0.150$. When the Ca amount "x" is less than 0.085, a phase transition temperature (hereinafter referred to as "$T_{to}$") from a tetragonal crystal to an orthorhombic crystal becomes higher than −20° C., with the result that the temperature dependence of the piezoelectric constant within the operating temperature range is increased.

Meanwhile, when the "x" is more than 0.150, Ca is not formed into a solid solution at a firing temperature of 1,400° C. or less, and hence CaTiO$_3$, which is an impurity phase, is generated, with the result that the piezoelectric constant is decreased.

The range of the Zr amount "y" is $0.025 \leq y \leq 0.085$. When the Zr amount "y" is less than 0.025, the piezoelectricity is lowered. When the "y" is more than 0.085, the phase transition temperature $T_{to}$ may be 0° C. or more. A piezoelectric material having a phase transition temperature $T_{to}$ of 0° C. or more has large temperature dependence of the piezoelectric constant within the operating temperature range.

When the Zr amount is 0.050 or more, an electromechanical coupling coefficient $k_{33}$ at room temperature can be improved to increase the piezoelectric constant. Accordingly, it is preferred that the range of the Zr amount "y" be $0.050 \leq y \leq 0.085$.

The range of the "a", which represents the ratio $\{a=(Ba+Ca)/(Zr+Ti)\}$ of the sum of the numbers of moles of the Ba and the Ca with respect to the sum of the numbers of moles of the Zr and the Ti, is $0.986 \leq a \leq 1.02$. When the "a" is less than 0.986, abnormal grain growth occurs at the time of firing. Further, an average grain size becomes more than 20 μm, and the mechanical strength of the material is decreased. When the "a" is more than 1.02, a high-density piezoelectric material is not obtained. When the density of the piezoelectric material is low, the piezoelectricity is decreased. In the present invention, the density of an insufficiently fired sample is smaller by 5% or more than that of a sufficiently fired high-density sample. In order to obtain a piezoelectric material having high density and high mechanical strength, the range of the "a" is $0.986 \leq a \leq 1.02$.

The piezoelectric material of the present invention contains, as a first sub-component, Mn in an amount of 0.04 part by mass or more and 0.36 part by mass or less in terms of a metal with respect to 100 parts by mass of the perovskite-type metal oxide. When Mn within the above-mentioned range is contained, a coercive electric field Ec is increased. However, when the content of Mn is less than 0.04 part by mass, the effect of increasing the coercive electric field Ec is not obtained. Meanwhile, when the content of Mn is more than 0.36 part by mass, the insulation resistance of the piezoelectric material is decreased. When the insulation resistance is low, a dielectric loss tangent at room temperature measured by applying an AC electric field having a frequency of 1 kHz and an electric field intensity of 10 V/cm through use of an impedance analyzer exceeds 0.010.

The dielectric loss tangent of the piezoelectric material of the present invention at a frequency of 1 kHz is preferably 0.010 or less. When the dielectric loss tangent is 0.010 or less, heat generation is small and a stable operation can be obtained even when an electric field of up to 500 V/cm is applied to the piezoelectric material under the driving conditions of an element.

Mn is not limited to metal Mn, only needs to be contained in the piezoelectric material as a Mn component, and may be contained in any form. For example, Mn may be formed into a solid solution at the B site or may be contained in a grain boundary. Alternatively, the Mn component may be contained in the piezoelectric material in the form of a metal, an ion, an oxide, a metal salt, a complex, or the like. More preferably, Mn is present from the viewpoints of an insulating property and ease of sintering. In general, the valence of Mn may be 4+, 2+, or 3+. The reason for this is as described below. When a conduction electron is present in a crystal (for example, when an oxygen defect is present in the crystal, when the A site is occupied by a donor element, or the like), the valence of Mn is decreased from 4+ to 3+, 2+, or the like, and thus the conduction electron is trapped, with the result that the insulation resistance can be improved.

Meanwhile, when the valence of Mn is less than 4+ such as 2+, Mn becomes an acceptor. When Mn is present in a perovskite structure crystal as an acceptor, holes are generated in the crystal or oxygen vacancies are formed in the crystal.

When the valence of Mn added in a large amount is 2+ or 3+, the holes cannot be fully compensated merely by the introduction of the oxygen vacancies, and the insulation resistance is decreased. Accordingly, most of Mn preferably has a valence of 4+. However, a significantly small amount of Mn may have a valence of less than 4+ and occupy the B site of the perovskite structure as an acceptor to form oxygen vacancies. This is because Mn having a valence of 2+ or 3+ and oxygen vacancies can form defective dipoles to improve the mechanical quality factor of the piezoelectric material. When trivalent Bi occupies the A site, Mn easily has a valence of less than 4+ in order to achieve charge balance.

The valence of Mn added in a slight amount to a non-magnetic (diamagnetic) material may be evaluated by measuring the temperature dependence of magnetic susceptibility. The magnetic susceptibility may be measured with a superconducting quantum interference device (SQUID), a vibrating-sample magnetometer (VSM), or a magnetic balance. The magnetic susceptibility $\chi$ obtained by the measurement generally follows the Curie-Weiss law represented by the expression (2).

$$\chi = C/(T-\theta) \quad (C: \text{Curie constant}, \theta: \text{paramagnetic Curie temperature})$$

Expression (2)

In general, Mn added in a slight amount to a non-magnetic material shows a spin S of 5/2 when having a valence of 2+, a spin S of 2 when having a valence of 3+, and a spin S of 3/2 when having a valence of 4+. Accordingly, the Curie constant C converted per unit Mn amount becomes a value corresponding to the value of the spin S at each valence of Mn. Thus, the average valence of Mn in the sample can be evaluated by deriving the Curie constant C from the temperature dependence of the magnetic susceptibility $\chi$.

In order to evaluate the Curie constant C, it is preferred to measure the temperature dependence of the magnetic susceptibility from the lowest possible temperature. The reason for this is as described below. The Mn amount is a slight amount, and hence the value of the magnetic susceptibility also becomes significantly small at a relatively high temperature such as the vicinity of room temperature, with the result that the measurement becomes difficult. The Curie constant C may be derived from the slope of a straight line when a reciprocal $1/\chi$ of the magnetic susceptibility is plotted against a temperature T and linearly approximated.

The piezoelectric material of the present invention contains, as a sub-component, Bi in an amount of 0.050 part by mass or more and 0.240 part by mass or less in terms of a metal with respect to 100 parts by mass of the perovskite-type metal oxide represented by the general formula (1). The content of Bi in the piezoelectric material may be measured by, for example, ICP-MS composition analysis, and when the content is below the measurement limit of 0.00001 part by mass, the content is regarded as 0 parts by mass. When the content of Bi is less than 0.050 part by mass, the effect of decreasing the phase transition temperature and improving the mechanical quality factor is not obtained. When the content of Bi is more than 0.050 part by mass, the electromechanical coupling coefficient is decreased by more than 30% as compared to the case in which Bi is not contained.

In the piezoelectric material of the present invention, Bi may be in a grain boundary or may be formed into a solid solution in the perovskite-type structure of $(Ba,Ca)(Ti,Zr)O_3$.

When Bi is present in the grain boundary, the friction between particles is reduced, and the mechanical quality factor is increased. When Bi is formed into a solid solution in $(Ba,Ca)(Ti,Zr)O_3$ having a perovskite structure, the $T_{ot}$ and the $T_{to}$ are decreased. Accordingly, the temperature dependence of the piezoelectric constant within the operating temperature range is lowered, and the mechanical quality factor can be further improved.

The position at which Bi is present may be evaluated by, for example, X-ray diffraction, electron diffraction, an electron microscope, ICP-MS, or the like.

When Bi is present at the B site, the lattice constant of the perovskite structure is increased because the ionic radius of Bi is larger than those of Ti and Zr.

When Bi is present at the A site, the optimum "a" value for firing a high-density ceramics becomes low. In a phase diagram of BaO and $TiO_2$, a liquid phase is present at high temperature on a $TiO_2$ rich side from a composition in which BaO and $TiO_2$ have a molar ratio of 1:1. Accordingly, in the case where $BaTiO_3$ ceramics is fired, when the ratio of a $TiO_2$ component is larger than the stoichiometric ratio, abnormal grain growth occurs due to liquid phase sintering. Meanwhile, when the ratio of a BaO component is large, sintering does not proceed easily, and the density of the ceramics is decreased. The presence of the Bi component at the A site may result in an excess of the A site component, which may rather make it difficult for the sintering of the ceramics to proceed. As a result, the density of the ceramics is decreased. In such a case, firing is allowed to proceed by devising a method of lowering the "a" value, and a high-density sample can be obtained.

The piezoelectric material of the present invention contains, as a sub-component, W in an amount of 0.100 part by mass or more and 0.380 part by mass or less in terms of a metal with respect to 100 parts by mass of the perovskite-type metal oxide. The content of W in the piezoelectric material may be measured by, for example, ICP-MS composition analysis, and when the content is below the measurement limit of 0.00001 part by mass, the content is regarded as 0 parts by mass.

When the content of W is less than 0.100 part by mass, a piezoelectric constant $d_{33}$ becomes smaller than those in the cases in which the content of W is 0.100 and W is not contained. When the content of W is more than 0.380 part by mass, the electromechanical coupling coefficient $k_{33}$ and the piezoelectric constant $d_{33}$ become small.

W is not limited to metal W, only needs to be contained in the piezoelectric material as a W component, and may be contained in any form. W is generally formed into a solid solution at the B site, but may be contained in a grain boundary. Alternatively, the W component may be contained in the piezoelectric material in the form of a metal, an ion, an oxide, a metal salt, a complex, or the like. In general, the valence of W may be 6+, and W enters the B site to act as a donor.

The ionic radius of W having entered the B site is smaller than those of Ti and Zr, and hence a c/a ratio of a tetragonal crystal becomes small, and the Curie temperature $T_C$ of the piezoelectric material that is a perovskite-type metal oxide is decreased. In addition, the influence at the phase transition point between the tetragonal crystal and the orthorhombic crystal is small. Because of this, a W ion having entered the B site as 6+ has an effect of reducing a tetragonal property, to thereby facilitate the polarization switching of the piezoelectricity to increase the piezoelectric constant.

In order to facilitate the manufacturing of the piezoelectric material of the present invention and adjust the physical properties of the piezoelectric material of the present invention, 1 mol % or less of Ba and Ca may be substituted with a divalent metal element such as Sr. Similarly, 1 mol % or less of Ti and Zr may be substituted with a tetravalent metal element such as Hf.

The density of the sintered body may be measured by, for example, the Archimedes method. In the present invention, when a ratio of measured density ($\rho_{meas}$) to theoretical density ($\rho_{calc.}$) obtained based on the composition and the lattice constant of the sintered impact, that is, relative density ($\rho_{calc.}/\rho_{meas}$) is 95% or more, it can be said that the relative density is sufficiently high as the piezoelectric material.

The Curie temperature $T_C$ refers to a temperature at or above which the piezoelectricity of the piezoelectric material is lost. Herein, a temperature at which the dielectric constant becomes maximum in the vicinity of a phase transition temperature between a ferroelectric phase (tetragonal phase) and a paraelectric phase (cubic phase) is defined as the Curie temperature $T_C$. The dielectric constant is measured, for example, by applying an AC electric field having a frequency of 1 kHz and an electric field intensity of 10 V/cm through use of an impedance analyzer.

The piezoelectric material of the present invention undergoes sequential phase transition from a rhombohedral crystal to an orthorhombic crystal, a tetragonal crystal, and a cubic crystal with an increase in temperature from low temperature. The "phase transition" as used herein refers exclusively to the phase transition from a tetragonal crystal to an orthorhombic crystal. The phase transition temperature may be evaluated by the same measurement method as in the Curie temperature, and the temperature at which the value obtained by differentiating a dielectric constant with a sample temperature is maximized is defined as the phase transition temperature. The crystal system may be evaluated by X-ray diffraction, electron diffraction, Raman scattering, or the like.

One of factors for decreasing the mechanical quality factor is the vibration of a domain wall. In general, as a domain structure becomes more complicated, the density of the domain wall is increased more, and the mechanical quality factor is decreased more. The crystal orientation of spontaneous polarization of the orthorhombic or tetragonal perovskite structure is <110> or <100> in pseudo-cubic notation, respectively. That is, the spatial degree of freedom of spontaneous polarization is lower in the tetragonal structure than in the orthorhombic structure. Because of this, the tetragonal structure has a simpler domain structure and a higher mechanical quality factor even when the composition is the same. Accordingly, it is preferred that the piezoelectric material of the present invention have a tetragonal structure rather than an orthorhombic structure within the operating temperature range.

In the vicinity of the phase transition temperature, the dielectric constant and the electromechanical coupling coefficient become maximum, and the Young's modulus becomes minimum. The piezoelectric constant is a function of those three parameters, which indicates a local maximum value or an inflection point in the vicinity of the phase transition temperature. Accordingly, when the phase transition is present within the operating temperature range of a device, the performance of the device is extremely fluctuated depending on the temperature, and the resonance frequency is fluctuated depending on the temperature, with the result that the control of the device may become difficult. Accordingly, it is desired that the phase transition, which is the largest factor for fluctuating the piezoelectric performance, be not within the operating temperature range. It is preferred that the phase transition temperature be farther away from the operating temperature range because the temperature dependence of the piezoelectric performance within the operating temperature range is lowered more.

The present invention enables only the Curie temperature to be decreased while maintaining the phase transition temperature between an orthorhombic crystal and a tetragonal crystal, in particular, by adding W. As a result, although the minimization of the piezoelectric constant $d_{33}$ has hitherto been remarkable, for example, between the local maximum values of the piezoelectric constant $d_{33}$ at the phase transition temperature, in particular, on a high temperature side (around 50° C.) of an operating temperature, when the Curie temperature approaches the high temperature side (around 50° C.), the decrease in piezoelectric constant $d_{33}$ on the high temperature side (around 50° C.) of the operating temperature region is suppressed, the temperature dependence is reduced, and the temperature stability is improved.

In this case, the change rate of the piezoelectric constant $d_{33}$ is represented by the following expression (3).

$$\text{Change rate of piezoelectric constant } d_{33}=(d_{33max}-d_{33min})/d_{33@RT} \quad \text{Expression (3)}$$

In the expression (3), the difference between the maximum value ($d_{33max}$) and the minimum value ($d_{33min}$) of the piezoelectric constant $d_{33}$ within the operating temperature range (for example, from 0° C. to 60° C.) is divided by the piezoelectric constant $d_{33}$ ($d_{33@RT}$) at room temperature. The change rate of the piezoelectric constant $d_{33}$ is preferably 0.3 or less, more preferably 0.23 or less. In this case, the piezoelectric constant $d_{33}$ at room temperature is preferably 240 pm/V or more from the viewpoint of exhibiting the performance of the device.

A method of manufacturing the piezoelectric material according to the present invention is not particularly limited.

When a piezoelectric ceramics is produced, a general procedure involving sintering solid powder, such as an oxide, a carbonate, a nitrate, or an oxalate, containing constituent elements under normal pressure may be adopted. The raw material therefor is formed of, for example, a metal compound, such as a Ba compound, a Ca compound, a Ti compound, a Zr compound, a Mn compound, a Bi compound, or a W compound.

Examples of the Ba compound that may be used include barium oxide, barium carbonate, barium oxalate, barium acetate, barium nitrate, barium titanate, barium zirconate, and barium zirconate titanate.

Examples of the Ca compound that may be used include calcium oxide, calcium carbonate, calcium oxalate, calcium acetate, calcium titanate, and calcium zirconate.

Examples of the Ti compound that may be used include titanium oxide, barium titanate, barium zirconate titanate, and calcium titanate.

Examples of the Zr compound that may be used include zirconium oxide, barium zirconate, barium zirconate titanate, and calcium zirconate.

Examples of the Mn compound that may be used include manganese carbonate, manganese monoxide, manganese dioxide, trimanganese tetraoxide, and manganese acetate.

Examples of the Bi compound that may be used include bismuth oxide.

Examples of the W compound that may be used include tungstate oxide and tungsten chloride.

In addition, there is no particular limitation on a raw material for adjusting the "a", which represents the ratio {a=(Ba+Ca)/(Zr+Ti)} of the sum of the numbers of moles of the Ba and the Ca with respect to the sum of the numbers of moles of the Zr and the Ti of the piezoelectric ceramics according to the present invention. The effect is the same irrespective of whether a Ba compound, a Ca compound, a Ti compound, or a Zr compound is used.

A method of granulating the raw material powder of the piezoelectric ceramics according to the present invention is not particularly limited. Examples of a binder that may be used in the granulation include polyvinyl alcohol (PVA), polyvinyl butyral (PVB), and an acrylic resin. The amount of the binder to be added is preferably from 1 part by mass to 10 parts by mass, more preferably from 2 parts by mass to 5 parts by mass from the viewpoint that the density of the compact increases. Mixed powder obtained by mechanically mixing the Ba compound, the Ca compound, the Ti compound, the Zr compound, the Mn compound, the Bi compound, and the W compound may be granulated. Those compounds may be calcined at a temperature of from about 800° C. to about 1,300° C. and then granulated. Alternatively, the Ba compound, the Ca compound, the Ti compound, the Zr compound, the Mn compound, and the Bi compound may be calcined, and then the W compound may be added simultaneously with the binder. The most preferred granulation method is a spray-drying method from the viewpoint that the grain size of the granulated powder can be made more uniform.

A method of producing a compact of a piezoelectric ceramics according to the present invention is not particularly limited. The compact refers to a solid substance formed of raw material powder, granulated powder, or a slurry. As means for producing the compact, uniaxial pressing, cold isostatic pressing, hot isostatic pressing, slip casting, extrusion molding, or the like may be used.

A method of sintering the piezoelectric ceramics according to the present invention is not particularly limited. Examples of the sintering method include sintering using an electric furnace, sintering using a gas furnace, a conduction heating method, a microwave sintering method, a millimeter-wave sintering method, and hot isostatic pressing (HIP). The electric furnace and the gas furnace for the sintering may each be a continuous furnace or a batch furnace.

A sintering temperature of the ceramics in the sintering method is not particularly limited, but is preferably a temperature at which each compound reacts to cause sufficient crystal growth. A sintering temperature is preferably 1,100° C. or more and 1,550° C. or less, more preferably 1,100° C. or more and 1,400° C. or less from the viewpoint of causing the grain size of the ceramics to fall within the range of from 2.0 μm or more and 12.0 μm or less. A piezoelectric ceramics sintered in the above-mentioned temperature range exhibits satisfactory piezoelectric performance.

In order to stabilize the properties of the piezoelectric ceramics to be obtained by the sintering treatment with good reproducibility, it is appropriate that the sintering treatment be performed with the sintering temperature being set constant in the above-mentioned range for 2 hours or more and 24 hours or less.

It is preferred that the piezoelectric ceramics be subjected to heat treatment at a temperature of 800° C. or more after subjected to polishing processing. When the piezoelectric ceramics is subjected to mechanical polishing processing, a residual stress is generated inside the piezoelectric ceramics.

However, when the piezoelectric ceramics be subjected to heat treatment at 1,000° C. or more to the extent that the surface roughness of a polished surface is not increased due to grain growth, the residual stress is relaxed, and the piezoelectric characteristics of the piezoelectric ceramics become further satisfactory.

In addition, the heat treatment also has an effect of eliminating raw material powder such as barium carbonate deposited in a grain boundary portion. The heat treatment time is not particularly limited, but is preferably 1 hour or more.

When the crystal grain size of the piezoelectric material of the present invention is more than 12.0 µm, there is a risk in that the material strength at the time of cutting processing and polishing processing may be insufficient. In addition, when the grain size is less than 2.0 µm, the piezoelectricity is lowered.

The "grain size" as used herein represents a "projected area equivalent circle diameter" generally referred to in a microscopic observation method, and represents a diameter of a perfect circle having the same area as that of the projected area of the crystal grain. In the present invention, a method of measuring a grain size is not particularly limited. For example, the grain size may be obtained by subjecting a photographic image, which is obtained by photographing the surface of a piezoelectric material with a polarizing microscope or a scanning electron microscope, to image processing. The optimum magnification varies depending on a target grain size, and hence an optical microscope and an electron microscope may be used properly depending on the case. The equivalent circle diameter may be obtained from an image of an abraded surface or a cross-section instead of the surface of a sintered body of a material.

When the piezoelectric material of the present invention is used as a film formed on a substrate, it is desired that the thickness of the piezoelectric material be 200 nm or more and 10 µm or less, more preferably 300 nm or more and 3 µm or less. This is because, when the film thickness of the piezoelectric material is set to 200 nm or more and 10 µm or less, a sufficient electromechanical converting function as a piezoelectric element is obtained.

A film forming method for the film is not particularly limited. Examples thereof include chemical solution deposition (CSD), a sol-gel process, metalorganic chemical vapor deposition (MOCVD), sputtering, pulse laser deposition (PLD), hydrothermal synthesis, and aerosol deposition (AD). Of those, chemical solution deposition or sputtering is the most preferred stacking method. The chemical solution deposition or the sputtering can easily increase the area of the film to be formed. It is preferred that the substrate to be used for the piezoelectric material of the present invention be a monocrystalline substrate cut and polished along a (001) plane or a (110) plane. With the use of a monocrystalline substrate cut and polished along a specific crystal plane, a piezoelectric material film formed on the surface of the substrate can also be strongly oriented in the same direction.

In the present invention, a piezoelectric material refers to the above-mentioned sintered body, film, or the like having a certain form containing a piezoelectric material.

Now, a piezoelectric element using the piezoelectric material of the present invention is described.

FIG. 1 is a schematic view for illustrating the configuration of a piezoelectric element according to one embodiment of the present invention. The piezoelectric element according to the present invention is characterized by including at least a first electrode 1, a piezoelectric material portion 2, and a second electrode 3, in which the piezoelectric material portion 2 is formed of the piezoelectric material of the present invention.

The piezoelectric characteristics of the piezoelectric material of the present invention may be evaluated by forming the piezoelectric element including at least the first electrode 1 and the second electrode 3. The first electrode 1 and the second electrode 3 are each formed of a conductive layer having a thickness of from about 5 nm to about 10 µm. A material therefor is not particularly limited, and only needs to be one to be generally used for a piezoelectric element. Examples thereof may include metals, such as Ti, Pt, Ta, Ir, Sr, In, Sn, Au, Al, Fe, Cr, Ni, Pd, Ag, and Cu, and compounds thereof.

Each of the first electrode 1 and the second electrode 3 may be formed of one kind of those materials, or may be obtained by stacking two or more kinds thereof. In addition, the first electrode 1 and the second electrode 3 may be formed of materials different from each other.

A manufacturing method for each of the first electrode 1 and the second electrode 3 is not limited. Those electrodes may each be formed by baking a metal paste or by sputtering, vapor deposition, or the like. In addition, both the first electrode 1 and the second electrode 3 may be patterned in desired shapes before use.

The piezoelectric element has polarization axes aligned in a certain direction. When the polarization axes are aligned in a certain direction, the piezoelectric constant of the piezoelectric element is increased.

A polarization method for the piezoelectric element is not particularly limited. The polarization treatment may be performed in the air or may be performed in silicone oil. A temperature at which the polarization is performed is preferably a temperature of from 60° C. to 150° C. However, an optimum condition slightly varies depending on the composition of a piezoelectric material forming the element. An electric field to be applied for performing the polarization treatment is preferably from 600 V/mm to 2.0 kV/mm.

The piezoelectric constants $d_{33}$ and $d_{31}$ and the electromechanical quality factors $k_{33}$ and $k_{31}$ of the piezoelectric element may be calculated from measurement results of a resonance frequency and an antiresonance frequency obtained through use of a commercially available impedance analyzer based on the Japan Electronics and Information Technology Industries Association standards (JEITA EM-4501). This method is hereinafter referred to as "resonance-antiresonance method".

Next, a multilayered piezoelectric element using the piezoelectric material of the present invention is described. (Multilayered Piezoelectric Element)

The multilayered piezoelectric element according to the present invention is characterized by including a plurality of piezoelectric material layers and a plurality of electrodes including an internal electrode alternately stacked, in which the piezoelectric material layers are each formed of the piezoelectric material of the present invention.

Figure 2A:
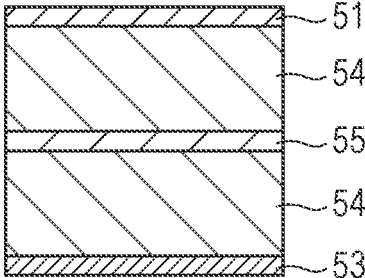
FIG. 2A is a schematic sectional view for illustrating the configuration of a multilayered piezoelectric element according to one embodiment of the present invention.
Figure 2B:
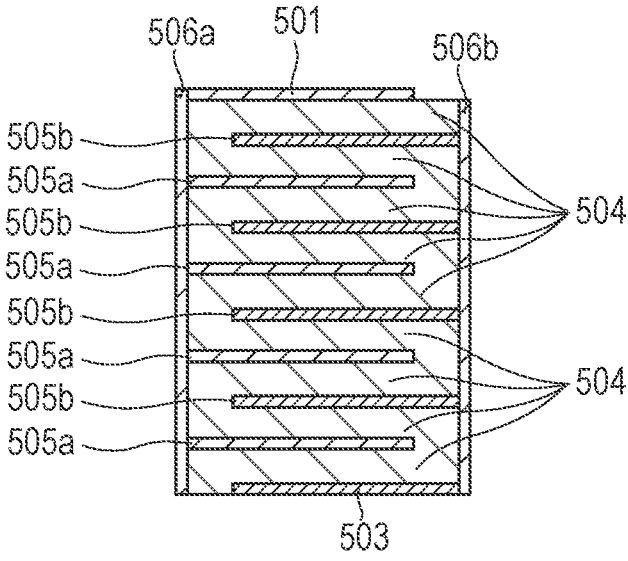
FIG. 2B is a schematic sectional view for illustrating the configuration of a multilayered piezoelectric element according to one embodiment of the present invention.

FIG. 2A and FIG. 2B are each a schematic sectional view for illustrating the configuration of the multilayered piezoelectric element according to one embodiment of the present invention. The multilayered piezoelectric element according to the present invention is characterized by including piezoelectric material layers 54 and electrodes including an internal electrode 55, the piezoelectric material layers 54 and the electrodes in a layered form being alternately stacked, in which the piezoelectric material layers 54 are each formed of the above-mentioned piezoelectric material. The electrode may include external electrodes, such as a first electrode 51 and a second electrode 53, in addition to the internal electrode 55.

FIG. 2A is an illustration of the configuration of the multilayered piezoelectric element of the present invention in which two layers of the piezoelectric material layers 54 and one layer of the internal electrode 55 are alternately stacked, and the multilayered structure is sandwiched between the first electrode 51 and the second electrode 53. As illustrated in FIG. 2B, the numbers of the piezoelectric material layers and the internal electrodes may be increased, and the numbers of the layers are not limited. The multilayered piezoelectric element of FIG. 2B has a configuration in which nine layers of the piezoelectric material layers 504 and eight layers of the internal electrodes 505 are alternately stacked, and the multilayered structure is sandwiched between the first electrode 501 and the second electrode 503, and includes an external electrode 506a and an external electrode 506b for short-circuiting the alternately formed internal electrodes.

The internal electrodes 55 and 505, the external electrodes 506a and 506b do not need to be identical in size and shape to the piezoelectric material layers 54 and 504, and may each be divided into a plurality of portions.

The internal electrodes 55 and 505, the external electrodes 506a and 506b, the first electrodes 51 and 501, and the second electrodes 53 and 503 are each formed of a conductive layer having a thickness of from about 5 nm to about 10 μm. A material for each of the electrodes is not particularly limited and only needs to be one to be generally used for a piezoelectric element. Examples thereof may include metals, such as Ti, Pt, Ta, Ir, Sr, In, Sn, Au, Al, Fe, Cr, Ni, Pd, Ag, and Cu, and compounds thereof. Each of the internal electrodes 55 and 505 and the external electrodes 506a and 506b may be formed of one kind thereof, may be formed of a mixture or alloy of two or more kinds thereof, or may be formed of a multilayered body of two or more kinds thereof. In addition, a plurality of electrodes may be respectively formed of materials different from each other. From the viewpoint that an electrode material is inexpensive, it is preferred that the internal electrodes 55 and 505 each contain at least any one kind selected from the group consisting of: Ni; and Cu. When at least any one kind selected from the group consisting of: Ni; and Cu is used for each of the internal electrodes 55 and 505, the multilayered piezoelectric element of the present invention is preferably fired in a reducing atmosphere.

In the multilayered piezoelectric element of the present invention, it is preferred that the internal electrode contain Ag and Pd, and a mass ratio M1/M2 between a content mass M1 of the Ag and a content mass M2 of the Pd is $0.25 \leq M1/M2 \leq 4.0$. It is not preferred that the mass ratio M1/M2 be less than 0.25 because the sintering temperature of the internal electrodes becomes high. Meanwhile, it is not preferred that the mass ratio M1/M2 be more than 4.0 because the internal electrodes are formed into an island shape, resulting in in-plane non-uniformity. The mass ratio M1/M2 is more preferably $0.3 \leq M1/M2 \leq 3.0$.

As illustrated in FIG. 2B, a plurality of electrodes including the internal electrodes 505 may be short-circuited to each other for the purpose of making the phases of their driving voltages uniform. For example, the internal electrode 505a and the first electrode 501 may be short-circuited through the external electrode 506a. The internal electrode 505b and the second electrode 503 may be short-circuited through the external electrode 506b. The internal electrode 505a and the internal electrode 505b may be alternately arranged. In addition, a mode in which the electrodes are short-circuited to each other is not limited. An electrode or wiring for short-circuiting may be arranged on a side surface of the multilayered piezoelectric element, or the electrodes may be short-circuited to each other by forming a through-hole passing through the piezoelectric material layers 504 and arranging a conductive material inside the through-hole.

(Liquid Discharge Head)

A liquid discharge head according to the present invention is characterized by including at least: a liquid chamber including a vibration unit including the piezoelectric element or the multilayered piezoelectric element; and a discharge port communicating to the liquid chamber. A liquid to be discharged by the liquid discharge head of the present invention is not particularly limited as long as the liquid is a fluid, and aqueous liquids such as water, ink, and fuel and nonaqueous liquids can be discharged.

Figure 3A:
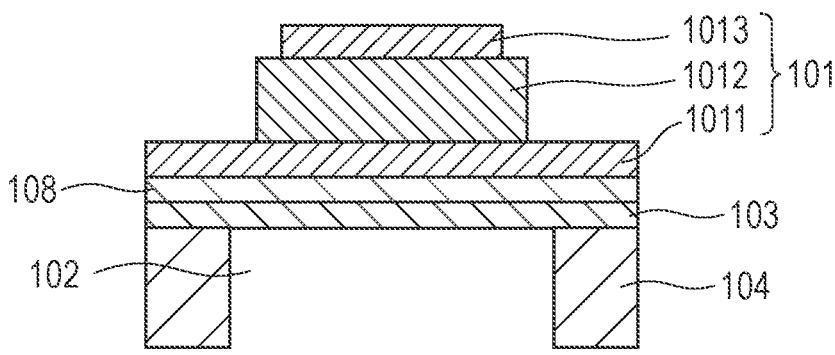
FIG. 3A is a schematic view for illustrating the configuration of a liquid discharge head according to one embodiment of the present invention.
Figure 3B:
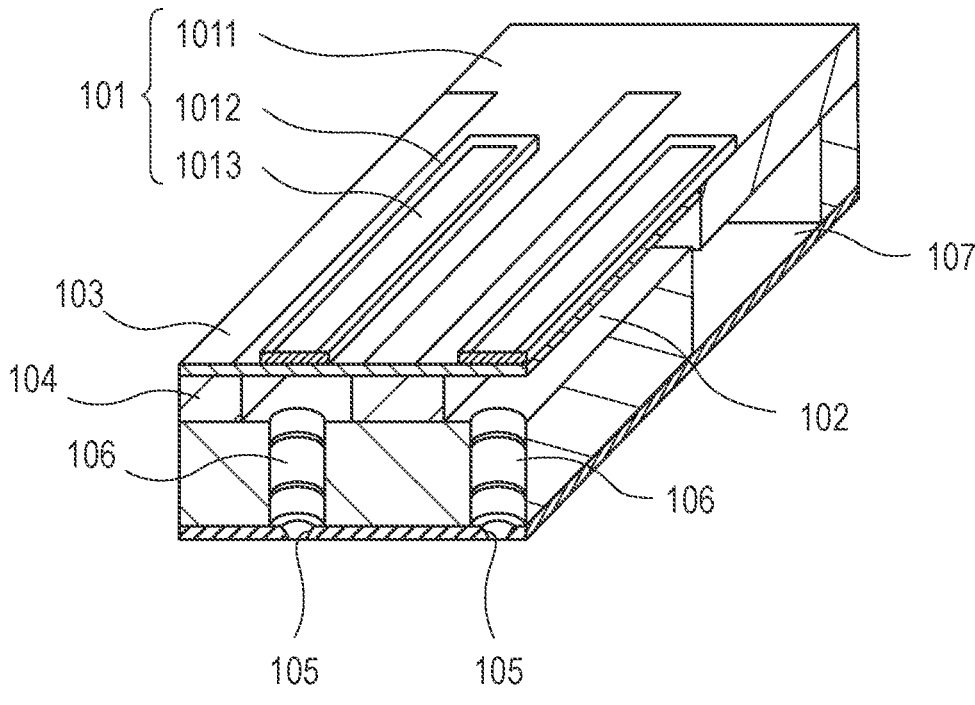
FIG. 3B is a schematic view for illustrating the configuration of the liquid discharge head according to one embodiment of the present invention.

FIG. 3A and FIG. 3B are each a schematic view for illustrating the configuration of the liquid discharge head according to one embodiment of the present invention. As illustrated in FIG. 3A and FIG. 3B, the liquid discharge head of the present invention is a liquid discharge head including a piezoelectric element 101 of the present invention. The piezoelectric element 101 is a piezoelectric element including at least a first electrode 1011, a piezoelectric material 1012, and a second electrode 1013. The piezoelectric material 1012 is patterned as required as illustrated in FIG. 3B.

FIG. 3B is a schematic view of the liquid discharge head. The liquid discharge head includes discharge ports 105, individual liquid chambers 102, communicating holes 106 for connecting the individual liquid chambers 102 and the discharge ports 105, liquid chamber partition walls 104, a common liquid chamber 107, a diaphragm 103, and the piezoelectric element 101. In FIG. 3B, the piezoelectric element 101 has a rectangular shape, but the shape thereof may be those other than the rectangle, such as an ellipse, a circle, and a parallelogram. In general, the piezoelectric material 1012 has a shape in conformity with the shape of the individual liquid chamber 102.

The vicinity of the piezoelectric element 101 included in the liquid discharge head of the present invention is described in detail with reference to FIG. 3A. FIG. 3A is a sectional view in a width direction of the piezoelectric element illustrated in FIG. 3B. Although the sectional shape of the piezoelectric element 101 is illustrated as a rectangle, the sectional shape may be a trapezoid or an inverted trapezoid.

In those figures, the first electrode 1011 is used as a lower electrode, and the second electrode 1013 is used as an upper electrode. However, the arrangement of the first electrode 1011 and the second electrode 1013 is not limited thereto. For example, the first electrode 1011 may be used as a lower electrode or may be used as an upper electrode. Similarly, the second electrode 1013 may be used as an upper electrode or may be used as a lower electrode. In addition, a buffer layer 108 may be present between the diaphragm 103 and the lower electrode. The difference in names is caused by the manufacturing method for the device, and the effect of the present invention can be obtained in any case.

In the liquid discharge head, the diaphragm 103 is fluctuated up and down due to the expansion and contraction of the piezoelectric material 1012 and applies a pressure to the liquid in the individual liquid chamber 102. As a result, the liquid is discharged from the discharge port 105. The liquid discharge head of the present invention can be used for printer applications and manufacturing of electronic apparatus. The thickness of the diaphragm 103 is 1.0 μm or more and 15 μm or less, preferably 1.5 μm or more and 8 μm or less. The material of the diaphragm is not limited, but is preferably Si. Si of the diaphragm may be doped with boron or phosphorus. In addition, the buffer layer and the electrodes on the diaphragm may be part of the diaphragm. The thickness of the buffer layer 108 is 5 nm or more and 300 nm or less, preferably 10 nm or more and 200 nm or less. The size of the discharge port 105 is 5 μm or more and 40 μm or less in terms of an equivalent circle diameter. The shape of the discharge port 105 may be a circle, a star shape, a square shape, or a triangle.

(Liquid Discharge Device)

Next, a liquid discharge device of the present invention is described. The liquid discharge device of the present invention includes a transfer material-carrying unit and the liquid discharge head.

Figure 4:
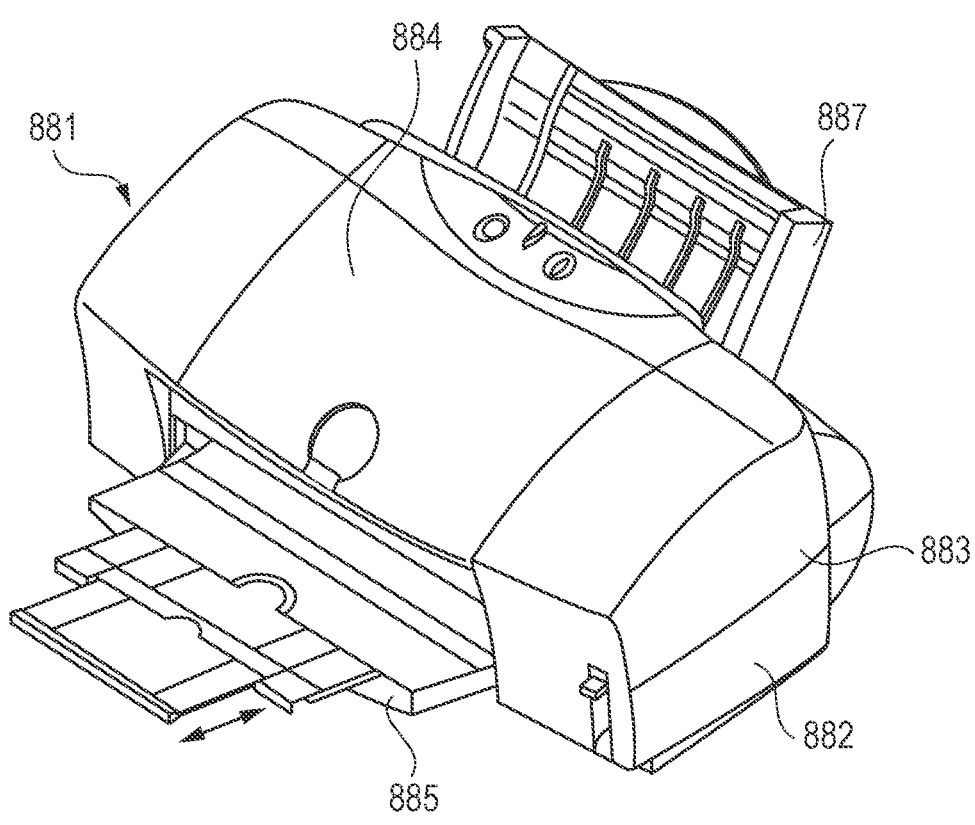
FIG. 4 is a schematic view for illustrating a liquid discharge device according to one embodiment of the present invention.
Figure 5:
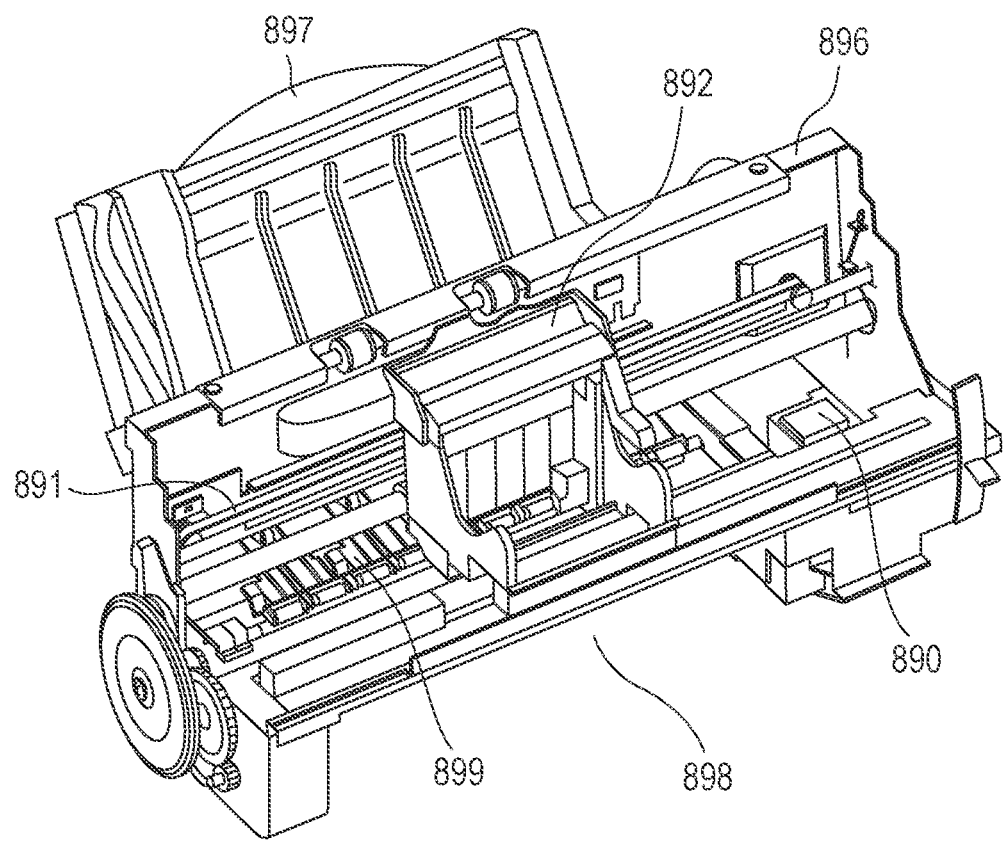
FIG. 5 is a schematic view for illustrating the liquid discharge device according to one embodiment of the present invention.

As an example of the liquid discharge device of the present invention, there may be given an ink jet recording apparatus illustrated in FIG. 4 and FIG. 5. In FIG. 5, there is illustrated a state in which exteriors 882 to 885 and 887 of a liquid discharge device (ink jet recording apparatus) 881 illustrated in FIG. 4 are removed. The ink jet recording apparatus 881 includes an automatic feeding unit 897 that automatically feeds a recording sheet serving as a transfer material into an apparatus main body 896. Further, the ink jet recording apparatus 881 includes a conveying unit 899 that guides the recording sheet fed from the automatic feeding unit 897 to a predetermined recording position and guides the recording sheet from the recording position to a delivery port 898, a recording unit 891 that performs recording on the recording sheet conveyed to the recording position, and a recovery unit 890 that performs a recovery process on the recording unit 891. The recording unit 891 includes a carriage 892 in which the liquid discharge head of the present invention is housed, and which is reciprocated on a rail.

In such ink jet recording apparatus, the carriage 892 is transferred on a rail by an electric signal transmitted from a computer, and when a driving voltage is applied to electrodes sandwiching the piezoelectric material, the piezoelectric material is displaced. Due to the displacement of the piezoelectric material, the individual liquid chamber 102 is pressurized through the diaphragm 103 illustrated in FIG. 3B, and ink is discharged from the discharge port 105 to perform printing. In the liquid discharge device of the present invention, the liquid can be uniformly discharged at a high speed.

In the example described above, a printer is exemplified. However, the liquid discharge device of the present invention may be used as a printing apparatus such as an ink jet recording apparatus, for example, a facsimile, a multifunctional peripheral, or a copying machine, or as an industrial liquid discharge device or a drawing apparatus for an object.

In addition, a user may select a desired transfer material depending on applications. A configuration in which the liquid discharge head moves relative to the transfer material carried on a stage serving as the carrying unit may be adopted.

(Ultrasonic Motor)

Figure 6A:
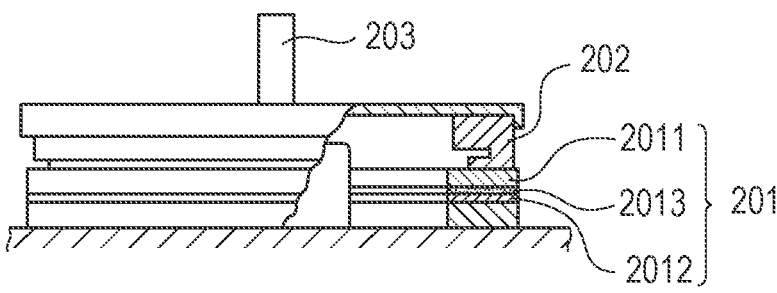
FIG. 6A is a schematic view for illustrating the configuration of an ultrasonic motor according to one embodiment of the present invention.
Figure 6B:
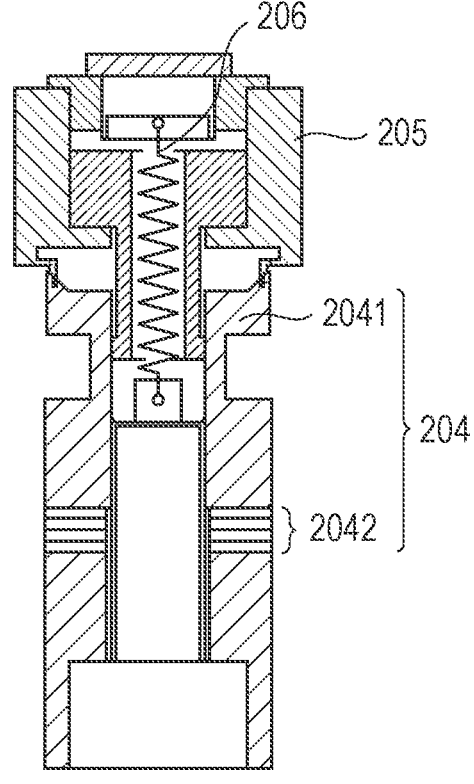
FIG. 6B is a schematic view for illustrating the configuration of an ultrasonic motor according to one embodiment of the present invention.

An ultrasonic motor according to the present invention is characterized by including at least: a vibrating body including the piezoelectric element or the multilayered piezoelectric element; and a moving body to be brought into contact with the vibrating body. FIG. 6A and FIG. 6B are each a schematic view for illustrating the configuration of an ultrasonic motor according to one embodiment of the present invention. FIG. 6A is an illustration of an ultrasonic motor in which the piezoelectric element of the present invention is formed of a single plate. The ultrasonic motor includes an oscillator 201, a rotor 202, which is brought into contact with the sliding surface of the oscillator 201 with a pressure applied by a pressurizing spring (not shown), and an output shaft 203 arranged so as to be integrated with the rotor 202. The oscillator 201 is formed of a metal elastic ring 2011, a piezoelectric element 2012 of the present invention, and an organic adhesive 2013 for bonding the piezoelectric element 2012 to the elastic ring 2011 (such as an epoxy- or cyanoacrylate-based adhesive). The piezoelectric element 2012 of the present invention is formed of a piezoelectric material sandwiched between a first electrode (not shown) and a second electrode (not shown). The application of two AC voltages different from each other in phase by an odd multiple of $\pi/2$ to the piezoelectric element of the present invention results in the generation of a flexural traveling wave in the oscillator 201, and hence each point on the sliding surface of the oscillator 201 undergoes an elliptical motion. When the rotor 202 is brought into press contact with the sliding surface of the oscillator 201, the rotor 202 receives a frictional force from the oscillator 201 to rotate in the direction opposite to the flexural traveling wave. A body to be driven (not shown) is joined to the output shaft 203, and is driven by the rotary force of the rotor 202. The application of a voltage to the piezoelectric material results in the expansion and contraction of the piezoelectric material due to a transverse piezoelectric effect. When an elastic body such as a metal is joined to the piezoelectric element, the elastic body is bent by the expansion and contraction of the piezoelectric material. The ultrasonic motor of the kind described in the foregoing utilizes this principle. Next, an ultrasonic motor including a piezoelectric element having a multilayered structure is illustrated in FIG. 6B. A vibrator 204 is formed of a multilayered piezoelectric element 2042 sandwiched between tubular metal elastic bodies 2041. The multilayered piezoelectric element 2042 is an element formed of a plurality of multilayered piezoelectric materials (not shown), and includes a first electrode and a second electrode on an outer surface of the stack and an internal electrode on an inner surface of the stack. The metal elastic bodies 2041 are fastened with bolts to fix the multilayered piezoelectric element 2042 therebetween to form the vibrator 204. The application of AC voltages different from each other in phase to the multilayered piezoelectric element 2042 causes the vibrator 204 to excite two vibrations orthogonal to each other. The two vibrations are combined to form a circular vibration for driving the tip portion of the vibrator 204. A constricted annular groove is formed in the upper portion of the vibrator 204 to enlarge the displacement of the vibration for driving. A rotor 205 is brought into contact with the vibrator 204 under pressure by a spring 206 for pressurization to obtain a frictional force for driving. The rotor 205 is rotatably supported by a bearing.

(Optical Apparatus)

Next, an optical apparatus of the present invention is described. The optical apparatus of the present invention is characterized by including a drive unit including the ultrasonic motor.

Figure 7A:
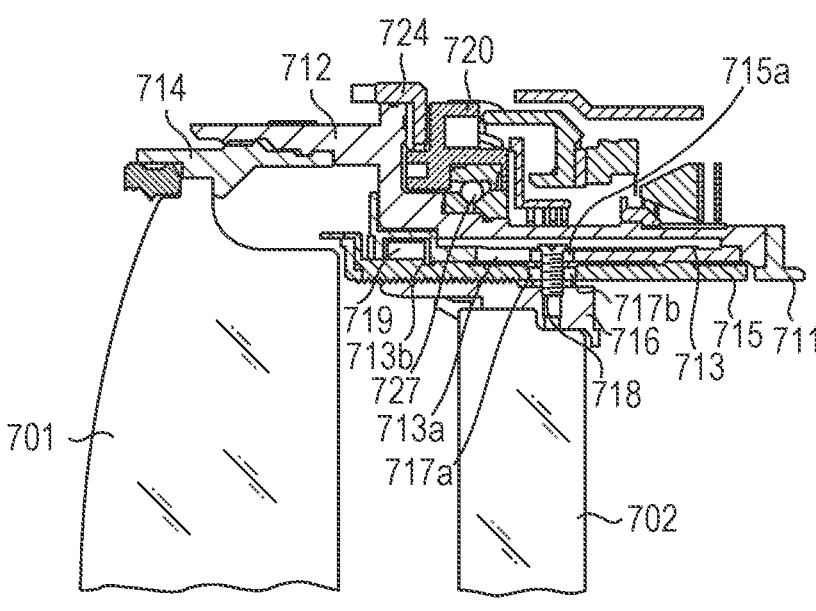
FIG. 7A is a schematic view for illustrating an optical apparatus according to one embodiment of the present invention.
Figure 7B:
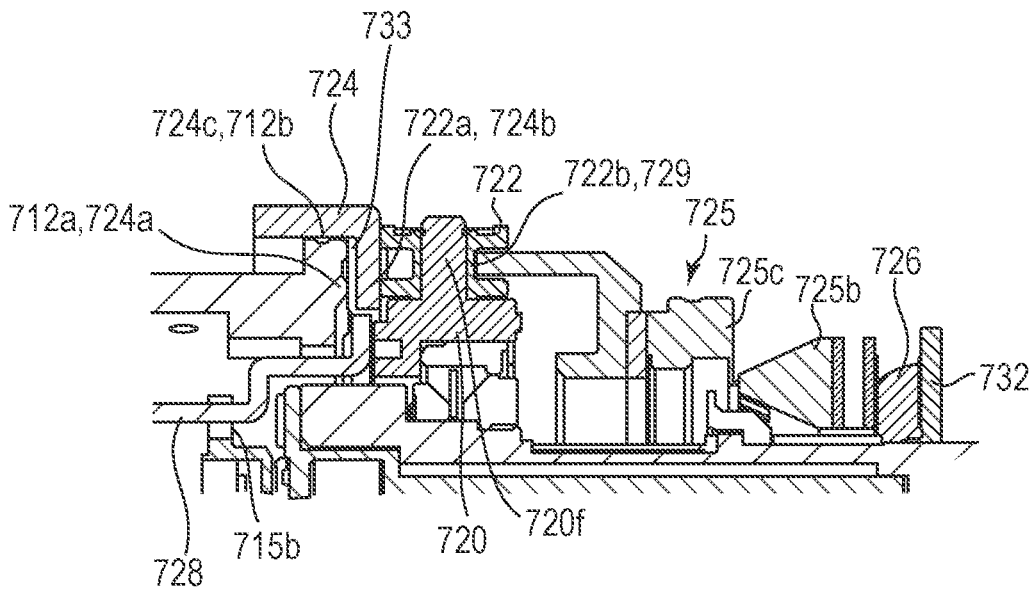
FIG. 7B is a schematic view for illustrating the optical apparatus according to one embodiment of the present invention.
Figure 8:
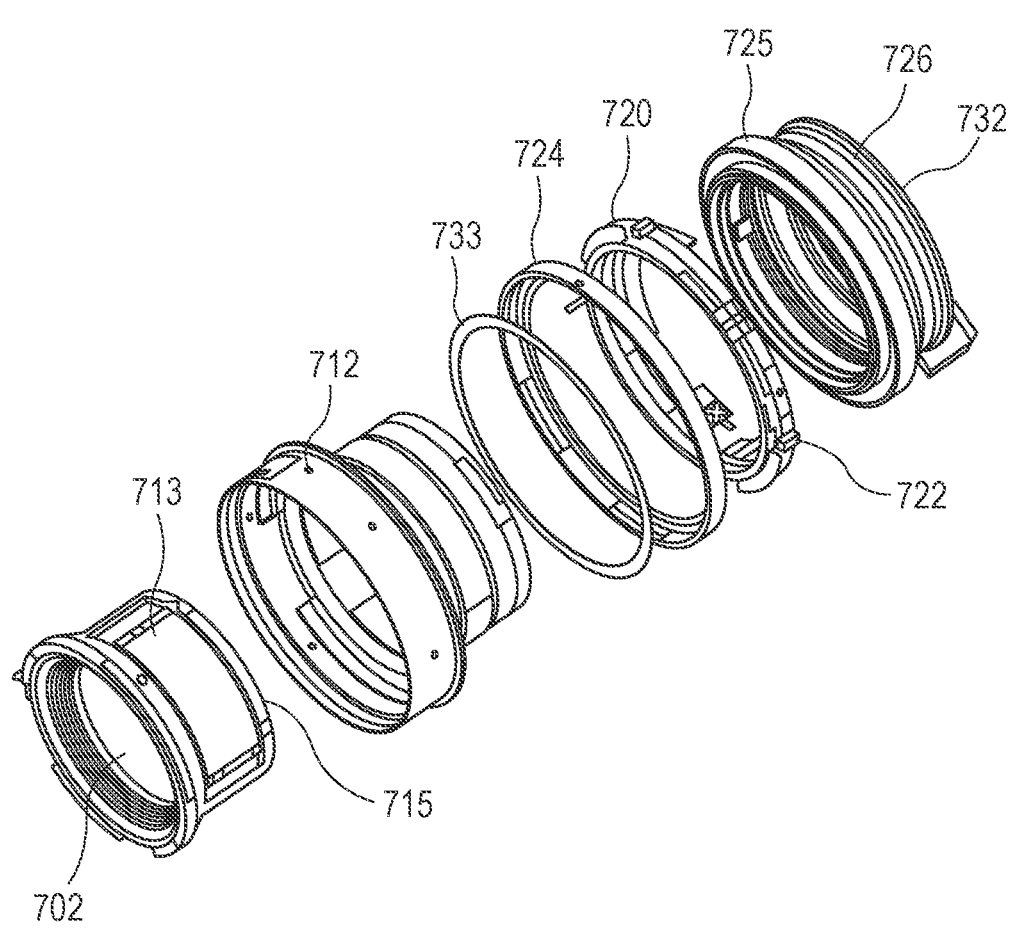
FIG. 8 is a schematic view for illustrating the optical apparatus according to one embodiment of the present invention.

FIG. 7A and FIG. 7B are each a sectional view of main parts of an interchangeable lens barrel for a single-lens reflex camera as an example of an optical apparatus according to an exemplary embodiment of the present invention. In addition, FIG. 8 is an exploded perspective view of the interchangeable lens barrel for the single-lens reflex camera as the example of the optical apparatus according to the exemplary embodiment of the present invention. A fixed barrel 712, a linear guide barrel 713, and a front unit barrel 714 are fixed to an attaching/detaching mount 711 for a camera. Those members are fixed members of the interchangeable lens barrel.

A linear guide groove 713a in an optical axis direction for a focus lens 702 is formed on the linear guide barrel 713. Cam rollers 717a and 717b protruding outward in a radial direction are fixed to a rear unit barrel 716 holding the focus lens 702 via axial screws 718, and the cam roller 717a is fitted in the linear guide groove 713a.

A cam ring 715 is fitted on the inner periphery of the linear guide barrel 713 in a rotatable manner. Relative movement between the linear guide barrel 713 and the cam ring 715 in the optical axis direction is restricted because a roller 719 fixed to the cam ring 715 is fitted in an annular groove 713b of the linear guide barrel 713. A cam groove 715a for the focus lens 702 is formed on the cam ring 715, and the above-mentioned cam roller 717b is simultaneously fitted in the cam groove 715a.

On the outer peripheral side of the fixed barrel 712, there is arranged a rotation transmission ring 720 held by a ball race 727 in a rotatable manner at a constant position with respect to the fixed barrel 712. The rotation transmission ring 720 has shafts 720f extending radially from the rotation transmission ring 720, and rollers 722 are held by the shafts 720f in a rotatable manner. A large diameter part 722a of the roller 722 is brought into contact with a mount side end surface 724b of a manual focus ring 724. In addition, a small diameter part 722b of the roller 722 is brought into contact with a joining member 729. Six rollers 722 are arranged on the outer periphery of the rotation transmission ring 720 at regular intervals, and each roller is arranged in the relationship as described above.

A low friction sheet (washer member) 733 is arranged on an inner diameter part of the manual focus ring 724, and this low friction sheet is sandwiched between a mount side end surface 712a of the fixed barrel 712 and a front side end surface 724a of the manual focus ring 724. In addition, an outer diameter surface of the low friction sheet 733 is formed in a ring shape so as to be circumferentially fitted on an inner diameter part 724c of the manual focus ring 724. Further, the inner diameter part 724c of the manual focus ring 724 is circumferentially fitted on an outer diameter part 712b of the fixed barrel 712. The low friction sheet 733 has a role of reducing friction in a rotation ring mechanism in which the manual focus ring 724 rotates relatively to the fixed barrel 712 about the optical axis.

The large diameter part 722a of the roller 722 is brought into contact with the mount side end surface 724b of the manual focus ring under a state in which a pressure is applied by a pressing force of a waved washer 726 pressing an ultrasonic motor 725 to the front of the lens. In addition, similarly, the small diameter part 722b of the roller 722 is brought into contact with the joining member 729 under a state in which an appropriate pressure is applied by a pressing force of the waved washer 726 pressing the ultrasonic motor 725 to the front of the lens. Movement of the waved washer 726 in the mount direction is restricted by a washer 732 connected to the fixed barrel 712 by bayonet joint. A spring force (biasing force) generated by the waved washer 726 is transmitted to the ultrasonic motor 725, and further to the roller 722, to be a force for the manual focus ring 724 to press the mount side end surface 712a of the fixed barrel 712. In other words, the manual focus ring 724 is integrated under a state in which the manual focus ring 724 is pressed to the mount side end surface 712a of the fixed barrel 712 via the low friction sheet 733.

Accordingly, when a control unit (not shown) drives the ultrasonic motor 725 to rotate with respect to the fixed barrel 712, the rollers 722 rotate about the shafts 720f because the joining member 729 is brought into frictional contact with the small diameter parts 722b of the rollers 722. As a result of the rotation of the rollers 722 about the shafts 720f, the rotation transmission ring 720 rotates about the optical axis (automatic focus operation).

In addition, when a manual operation input portion (not shown) gives a rotation force about the optical axis to the manual focus ring 724, the following action occurs. That is, the rollers 722 rotate about the shafts 720f by friction force because the mount side end surface 724b of the manual focus ring 724 is brought into contact by pressure to the large diameter parts 722a of the rollers 722. When the large diameter parts 722a of the rollers 722 rotate about the shafts 720f, the rotation transmission ring 720 rotates about the optical axis. In this case, the ultrasonic motor 725 does not rotate because of a friction retaining force between a rotor 725c and a stator 725b (manual focus operation).

Two focus keys 728 are mounted to the rotation transmission ring 720 at opposing positions, and the focus key 728 is fitted to a notch portion 715b arranged on the tip of the cam ring 715. Accordingly, when the automatic focus operation or the manual focus operation is performed so that the rotation transmission ring 720 is rotated about the optical axis, the rotation force is transmitted to the cam ring 715 via the focus key 728. When the cam ring is rotated about the optical axis, the rear unit barrel 716 whose rotation is restricted by the cam roller 717a and the linear guide groove 713a is moved forward and backward along the cam groove 715a of the cam ring 715 by the cam roller 717b. Thus, the focus lens 702 is driven, and the focus operation is performed.

While the interchangeable lens barrel for the single-lens reflex camera has been described as the optical apparatus of the present invention, the optical apparatus of the present invention can be applied to any optical apparatus including the drive unit including the ultrasonic motor, regardless of a type of the camera, including a compact camera, an electronic still camera, a personal digital assistant with a camera, and the like.

(Vibration Device and Dust Removing Device)

A vibration device used, for example, for conveying and removing particles, powder, and droplets are widely used in an electronic apparatus and the like.

Now, as an example of a vibration device of the present invention, a dust removing device using the piezoelectric element of the present invention is described.

A dust removing device according to the present invention is characterized by including a vibrating body including a diaphragm including the piezoelectric element or the multilayered piezoelectric element.

Figure 9A:
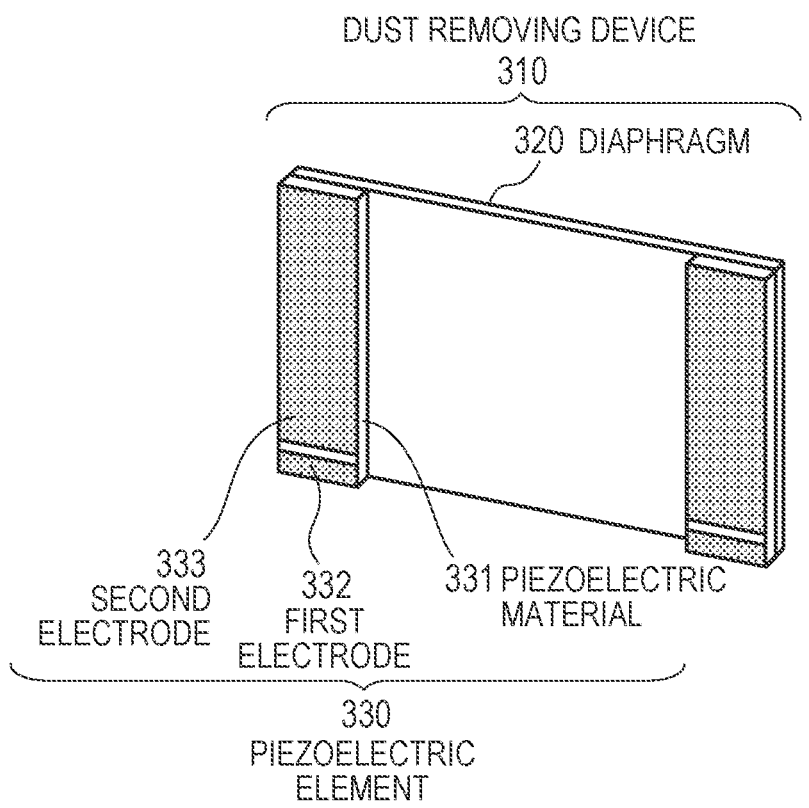
FIG. 9A is a schematic view for illustrating one embodiment in which a vibration device of the present invention is used as a dust removing device.
Figure 9B:
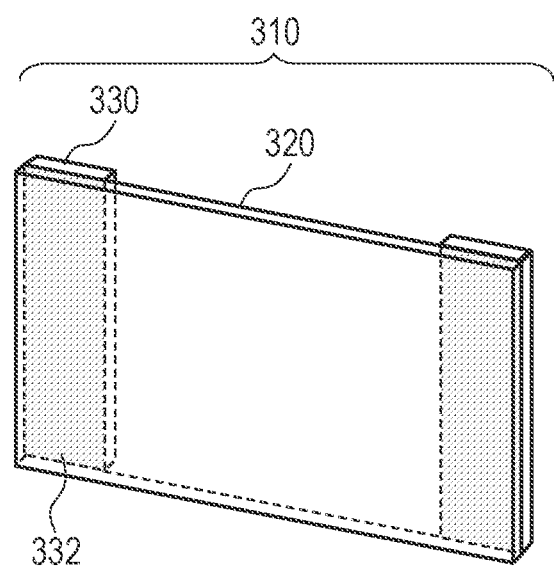
FIG. 9B is a schematic view for illustrating one embodiment in which the vibration device of the present invention is used as the dust removing device.

FIG. 9A and FIG. 9B are each a schematic view for illustrating a dust removing device according to one embodiment of the present invention. A dust removing device 310 includes plate-like piezoelectric elements 330 and a diaphragm 320. The piezoelectric element 330 may be the multilayered piezoelectric element of the present invention. A material for the diaphragm 320 is not limited. When the dust removing device 310 is used for an optical device, a light transmissive material or a light reflective material may be used as the diaphragm 320.

Figure 10:
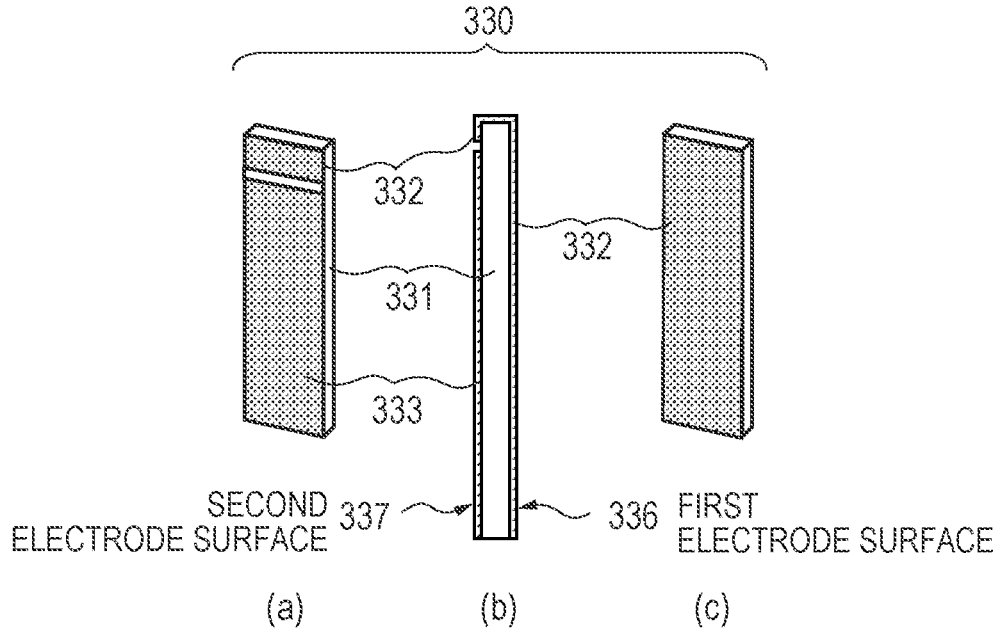
FIG. 10 is a schematic view for illustrating the configuration of a piezoelectric element in the dust removing device of the present invention.

(a), (b), and (c) of FIG. 10 are each a schematic view for illustrating the configuration of the piezoelectric element 330 in FIG. 9A and FIG. 9B. In (a) and (c) of FIG. 10, the configurations of front and back surfaces of the piezoelectric element 330 are illustrated. In (b) of FIG. 10, the configuration of a side surface is illustrated. As illustrated in FIG. 9A and FIG. 9B, the piezoelectric element 330 includes a piezoelectric material 331, a first electrode 332, and a second electrode 333, and the first electrode 332 and the second electrode 333 are each arranged so as to be opposed to a plate surface of the piezoelectric material 331. Similarly to FIG. 9A and FIG. 9B, the piezoelectric element 330 may be the multilayered piezoelectric element of the present invention. In this case, the piezoelectric material 331 has an alternate structure of a piezoelectric material layer and an internal electrode, and can provide driving waveforms different from each other in phase depending on layers of the piezoelectric material by short-circuiting the internal electrode with the first electrode 332 or the second electrode 333 alternately. In (c) of FIG. 10, a surface on which the first electrode 332 protruding in front of the piezoelectric element 330 is installed is defined as a first electrode surface 336, and in (a) of FIG. 10, a surface on which the second electrode 333 protruding in front of the piezoelectric element 330 is installed is defined as a second electrode surface 337.

Herein, the electrode surface in the present invention refers to the surface of the piezoelectric element on which the electrode is installed, and the first electrode 332 may wrap around the second electrode surface 337, for example, as illustrated in (a), (b), and (c) of FIG. 10.

As illustrated in FIG. 9A and FIG. 9B, in the piezoelectric elements 330 and the diaphragm 320, the first electrode surface 336 of each of the piezoelectric elements 330 is fixed to a plate surface of the diaphragm 320. Then, a stress is generated between the piezoelectric element 330 and the diaphragm 320 by driving the piezoelectric element 330, to thereby generate out-of-plane vibration in the diaphragm 320. The dust removing device 310 of the present invention is a device for removing foreign matter such as dust adhering to the surface of the diaphragm 320 through the out-of-plane vibration of the diaphragm 320. The out-of-plane vibration means elastic vibration that displaces the diaphragm into an optical axis direction, that is, a thickness direction of the diaphragm.

Figure 11:
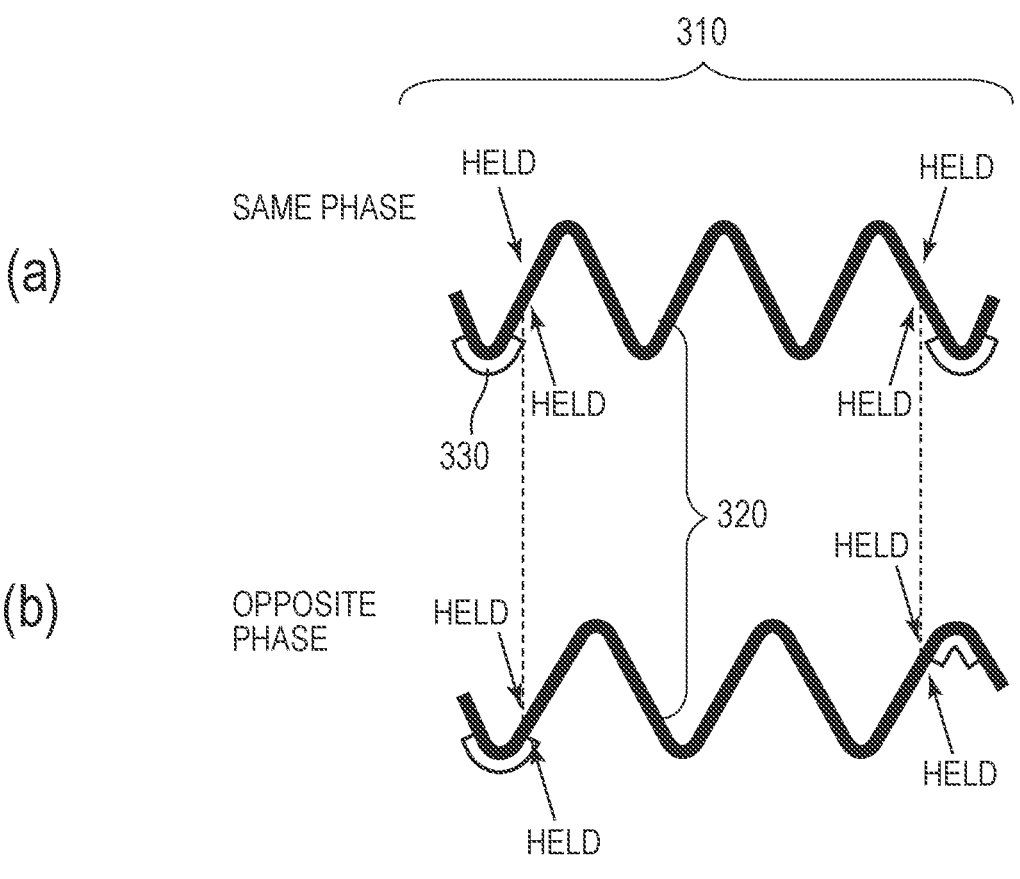
FIG. 11 is a schematic view for illustrating the vibration principle of the dust removing device of the present invention.

(a) and (b) of FIG. 11 are each a schematic view for illustrating the vibration principle of the dust removing device 310 of the present invention. In (a) of FIG. 11, there is illustrated a state in which the out-of-plane vibration is generated in the diaphragm 320 by applying AC voltages having the same phase to a pair of left and right piezoelectric elements 330, respectively. The polarization direction of the piezoelectric material forming the pair of left and right piezoelectric elements 330 is the same as the thickness direction of the piezoelectric elements 330, and the dust removing device 310 is driven in the seventh vibration mode. In (b) of FIG. 11, there is illustrated a state in which the out-of-plane vibration is generated in the diaphragm 320 by applying AC voltages having opposite phases that are opposite by 180° to the pair of left and right piezoelectric elements 330, respectively. The dust removing device 310 is driven in the sixth vibration mode. The dust removing device 310 of the present invention is a device capable of effectively removing dust adhering to the surface of the diaphragm by using at least two vibration modes properly depending on the case.

(Image Pickup Apparatus)

Figure 12:
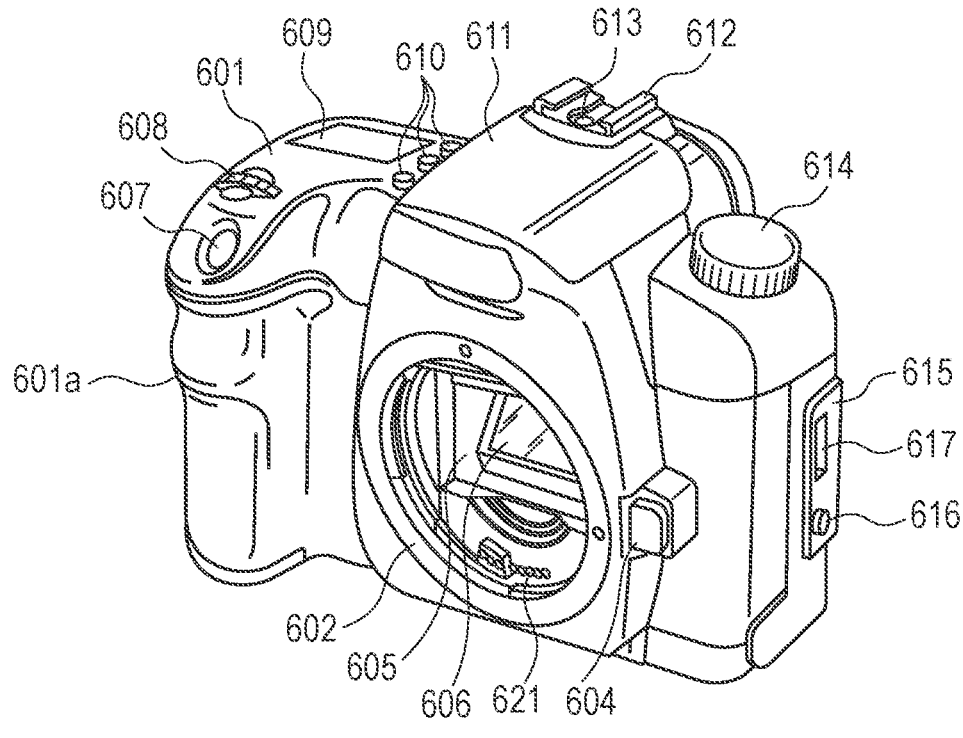
FIG. 12 is a schematic view for illustrating an image pickup apparatus according to one embodiment of the present invention.
Figure 13:
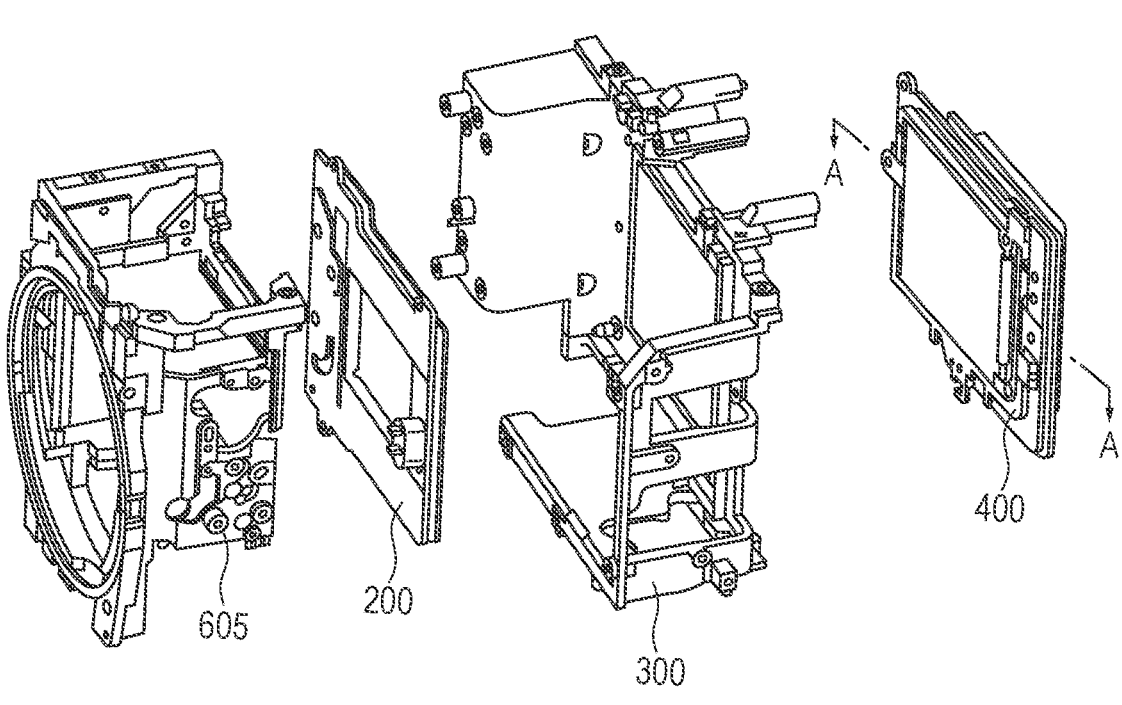
FIG. 13 is a schematic view for illustrating the image pickup apparatus according to one embodiment of the present invention.

Next, an image pickup apparatus of the present invention is described. The image pickup apparatus of the present invention is an image pickup apparatus including at least the dust removing device and an image pickup element unit, and is characterized in that the diaphragm of the dust removing device is provided on a light receiving surface side of the image pickup element unit. FIG. 12 and FIG. 13 are each a view for illustrating a digital single-lens reflex camera as an example of the image pickup apparatus according to an exemplary embodiment of the present invention.

FIG. 12 is a front side perspective view of a camera main body 601 when viewed from an object side, for illustrating a state in which a photographing lens unit is removed. FIG. 13 is an exploded perspective view of a schematic configuration of an inner portion of the camera for illustrating peripheral structures of the dust removing device of the present invention and an image pickup unit 400.

A mirror box 605 that guides a photographing luminous flux having passed through a photographing lens is provided in the camera main body 601, and a main mirror (quick return mirror) 606 is arranged in the mirror box 605. The main mirror 606 may have a state of being held at an angle of 45° with respect to a photographing optical axis in order to guide the photographing luminous flux in a direction of a penta dach mirror (not shown), and a state of being held at a position retracted from the photographing luminous flux in order to guide the photographing luminous flux in a direction of an image pickup element (not shown).

On the object side of a main body chassis 300 serving as a skeleton of the camera main body, the mirror box 605 and a shutter unit 200 are arranged in the stated order from the object side. In addition, the image pickup unit 400 is arranged on a photographer side of the main body chassis 300. The image pickup unit 400 is installed so that an image pickup surface of the image pickup element is adjusted to be parallel to a mounting surface of a mount portion 602 serving as a reference for mounting the photographing lens unit at a predetermined distance.

Herein, the digital single-lens reflex camera has been described as the image pickup apparatus of the present invention, but for example, a camera with an interchangeable photographing lens unit, such as a mirrorless digital single-lens camera without the mirror box 605, may be used. In addition, the image pickup apparatus of the present invention can also be applied to a device in which it is required to remove dust adhering to the surface of an optical component, in particular, among various image pickup apparatus, such as a video camera with an interchangeable photographing lens unit, a copying machine, a fax machine, and a scanner, or electronic and electrical devices including image pickup apparatus.

(Piezoelectric Acoustic Component)

Next, a piezoelectric acoustic component of the present invention is described. The piezoelectric acoustic component of the present invention is characterized by including the piezoelectric element or the multilayered piezoelectric element. The piezoelectric acoustic component encompasses a speaker, a buzzer, a microphone, and a surface acoustic wave (SAW) element.

(Electronic Apparatus)

Figure 14:
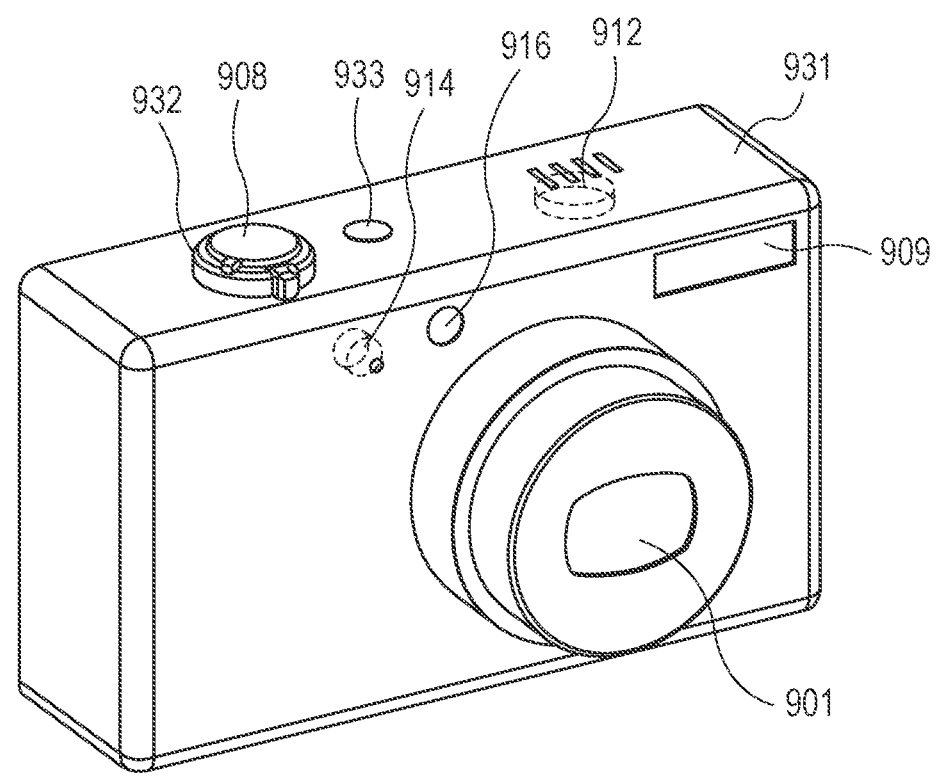
FIG. 14 is a schematic view for illustrating an electronic apparatus according to one embodiment of the present invention.

Next, an electronic apparatus of the present invention is described. The electronic apparatus of the present invention is characterized by including the piezoelectric acoustic component. FIG. 14 is a general perspective view of a main body 931 of a digital camera as an example of an electronic apparatus according to a preferred embodiment of the present invention, as viewed from the front.

An optical apparatus 901, a microphone 914, a strobo-scopic light emission unit 909, and a fill light unit 916 are arranged on a front surface of the main body 931. The microphone 914 is installed in the main body, and hence is illustrated by a broken line. In the front of the microphone 914, there is a hole shape provided for collecting external sound.

A power button 933, a speaker 912, a zoom lever 932, and a release button 908 for performing a focus operation are arranged on the top surface of the main body 931. The speaker 912 is installed in the main body 931, and hence is illustrated by a broken line. In the front of the speaker 912, there is a hole shape provided for transmitting sound to the outside.

The piezoelectric acoustic component of the present invention is used for at least one of the microphone 914, the speaker 912, or the surface acoustic wave element.

While the digital camera has been described as the electronic apparatus of the present invention, the electronic apparatus of the present invention can also be applied to various types of the electronic apparatus including the piezoelectric acoustic component, such as a sound reproduction device, a sound recording device, a cellular phone, or an information terminal.

(Ultrasonic Probe)

Next, an ultrasonic probe of the present invention is described. The ultrasonic probe of the present invention is characterized by including the piezoelectric element, in which the piezoelectric element transmits and receives a signal.

Figure 15:
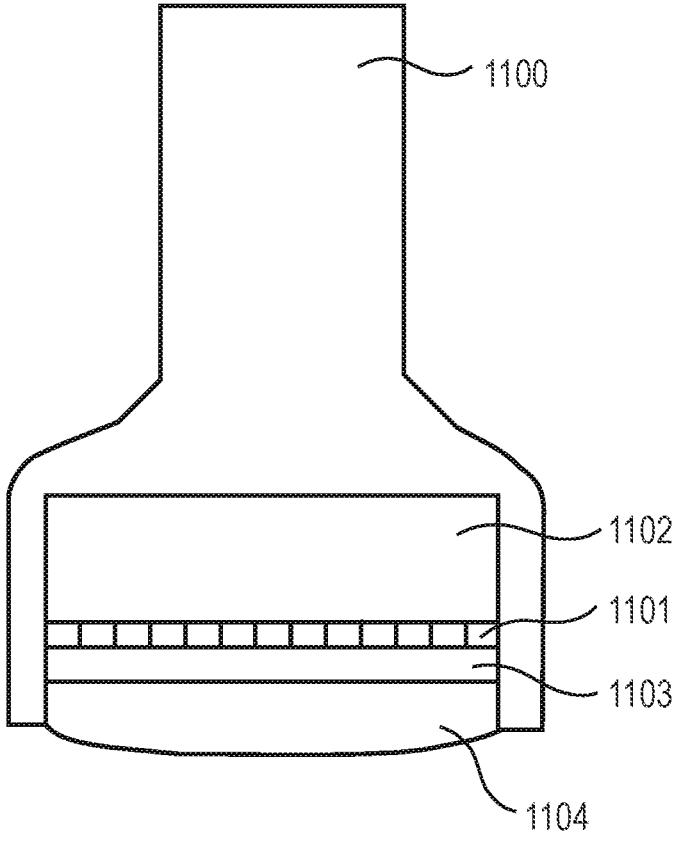
FIG. 15 is a schematic view for illustrating an ultrasonic probe according to one embodiment of the present invention.

FIG. 15 is a schematic sectional view for illustrating the ultrasonic probe according to one embodiment of the present invention.

An ultrasonic probe 1100 of FIG. 15 includes a plurality of piezoelectric elements 1101, a backing material 1102, an acoustic matching layer 1103, and an acoustic lens 1104. As illustrated in FIG. 15, the plurality of piezoelectric elements 1101 are arranged on the backing material 1102 so as to adhere thereto, and the acoustic matching layer 1103 that matches an acoustic impedance is formed on each surface serving as a transmitting/receiving surface of the piezoelectric elements 1101 on a side opposite to the backing material 1102.

The acoustic matching layer 1103 may be a single layer or a plurality of layers, preferably two or more layers. As a material to be used for the acoustic matching layer 1103, there may be used, for example, carbon, aluminum, an aluminum alloy (for example, an Al—Mg alloy), a magnesium alloy, Macor glass, glass, fused quartz, copper graphite, polyethylene, polypropylene, polycarbonate, an ABC resin, polyphenylene ether, an ABS resin, an AAS resin, an AES resin, nylon, polyamide imide, polyethylene terephthalate, polycarbonate, an epoxy resin, or a urethane resin.

In addition, as the backing material 1102, there may be used, for example, a thermoplastic resin, such as natural rubber, ferrite rubber, an epoxy resin, vinyl chloride, polyvinyl butyral, an ABS resin, polyurethane, polyvinyl alcohol, polyethylene, polypropylene, polyacetal, polyethylene terephthalate, a fluorine resin, polyethylene glycol, or polyethylene terephthalate, a product obtained by adding metal powder thereto, or a superhard material, such as tungsten carbide.

The piezoelectric element 1101 may be integrated or may be divided into a plurality of pieces. In FIG. 15, there is illustrated an example of a case in which the piezoelectric element 1101 is provided so as to be divided. A flexible cable (not shown) is connected to electrodes of the respective piezoelectric elements so that signals transmitted and received by the piezoelectric elements can be input and output. The acoustic lens 1104 adheres to the acoustic matching layer 1103. The acoustic lens 1104 is a member configured to converge ultrasonic waves transmitted from the piezoelectric elements 1101 toward the object, and has an arc shape in the example of FIG. 15. As a material for the acoustic lens 1104, for example, a rubber containing a silicone-based resin (rubber) as a main component is generally used.

When the ultrasonic probe 1100 is used, an AC voltage is applied to the piezoelectric elements 1101 through the flexible cable, and the piezoelectric elements 1101 are vibrated by the piezoelectric effect to transmit the ultrasonic waves from the piezoelectric elements 1101. In this case, when the acoustic impedance of the object which the ultrasonic waves are applied is small, or when the ultrasonic waves are applied to the object through water or air, reflected waves caused by a great change in acoustic impedance can be suppressed due to the presence of the acoustic matching layer 1103, and the ultrasonic waves to the object can be efficiently radiated thereto. Then, at the time of reception, the piezoelectric elements 1101 are vibrated with the ultrasonic waves reflected from the inside of the object, and this vibration is electrically converted by the piezoelectric effect to obtain a reception signal. At the time of transmission and reception, the conversion of electrical energy and mechanical energy is performed, and the conversion efficiency in this case depends on the magnitude of the electromechanical coupling coefficient.

(Ultrasonic Diagnostic System)

Figure 16:
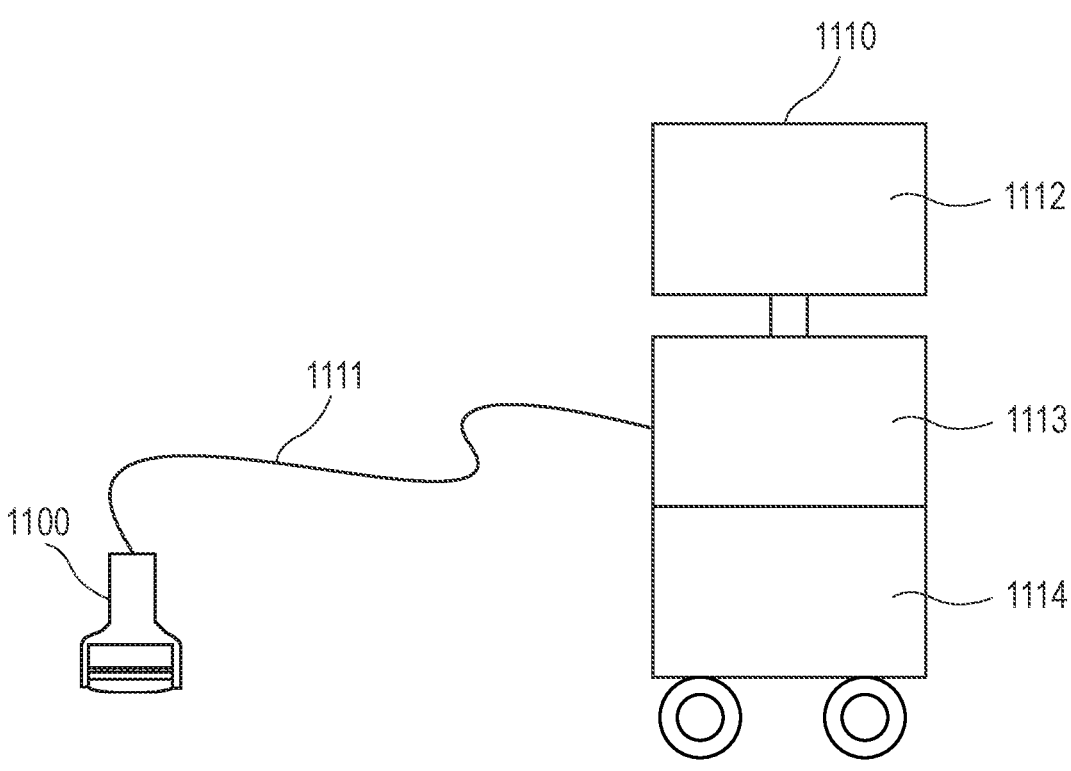
FIG. 16 is a schematic view for illustrating an ultrasonic diagnostic system according to one embodiment of the present invention.

Next, an ultrasonic diagnostic system of the present invention is described. The ultrasonic diagnostic system of the present invention is characterized by including at least: the ultrasonic probe; and an image output unit. FIG. 16 is a schematic view for illustrating an ultrasonic diagnostic apparatus according to one embodiment of the present invention. An ultrasonic diagnostic apparatus 1110 of FIG. 16 includes the ultrasonic probe 1100, a cable 1111, a drive control unit 1113, an image output unit 1112, and an image processing unit 1114. The flexible cable of the ultrasonic probe 1100 and the drive control unit 1113 are connected to each other through the cable 1111, and an AC voltage is applied from the drive control unit 1113 to the piezoelectric elements 1101 of the ultrasonic probe 1100 through the cable 1111. When the ultrasonic waves are radiated to the inside of the object from the ultrasonic probe 1100, the ultrasonic waves reflected from the inside of the object are converted into electric signals again by the ultrasonic probe 1100 and input to an image processing unit 1114 through the cable 1111. In the image processing unit 1114, image data is created through calculation from changes in delay time and signal intensity with respect to the AC voltage output from the drive control unit 1113. The created image data is output to the image output unit 1112.

In addition, in FIG. 16, an electric signal of the ultrasonic probe 1100 is input to the image processing unit 1114 through the cable 1111. However, an electric signal may be input to the image processing unit 1114 via radio. Further, the image processing may be performed at a distance via a network line without installing the image processing unit 1114 at a site in which the ultrasonic probe 1100 is used for diagnosis. Similarly, the image output unit 1112 may be distant via radio or be distant via a network line.

As described above, the piezoelectric element and the multilayered piezoelectric element of the present invention is suitably used in a liquid discharge head, a liquid discharge device, an ultrasonic motor, an optical apparatus, a vibration device, a dust removing device, an image pickup apparatus, a piezoelectric acoustic component, an electronic apparatus, an ultrasonic probe, and an ultrasonic diagnostic system.

Through use of the piezoelectric element and the multilayered piezoelectric element of the present invention, there can be provided a liquid discharge head having a nozzle density and a discharge speed comparable to or higher than those in the case of using a piezoelectric element containing lead.

Through use of the liquid discharge head of the present invention, there can be provided a liquid discharge device having a discharge speed and discharge accuracy comparable to or higher than those in the case of using a piezoelectric element containing lead.

Through use of the piezoelectric element of the present invention, there can be provided a vibration actuator including: a vibrating body including the piezoelectric element; and a contact body to be brought into contact with the vibrating body.

Through use of the piezoelectric element or the multilayered piezoelectric element of the present invention, there can be provided an ultrasonic motor having a driving force and durability comparable to or higher than those in the case of using a piezoelectric element containing lead.

Through use of the ultrasonic motor of the present invention, there can be provided an optical apparatus having durability and operating accuracy comparable to or higher than those in the case of using a piezoelectric element containing lead.

Through use of the piezoelectric element or the multilayered piezoelectric element of the present invention, there can be provided a vibration device having vibration ability and durability comparable to or higher than those in the case of using a piezoelectric element containing lead.

Through use of the vibration device of the present invention, there can be provided a dust removing device having dust removing efficiency and durability comparable to or higher than those in the case of using a piezoelectric element containing lead.

Through use of the dust removing device of the present invention, there can be provided an image pickup apparatus having a dust removing function comparable to or higher than that in the case of using a piezoelectric element containing lead.

Through use of the piezoelectric acoustic component including the piezoelectric element or the multilayered piezoelectric element of the present invention, there can be provided an electronic apparatus having soundability comparable to or higher than that in the case of using a piezoelectric element containing lead.

Through use of the piezoelectric element of the present invention, there can be provided an ultrasonic probe having transmitting/receiving performance comparable to or higher than that in the case of using a piezoelectric element containing lead.

In addition, there can be provided an ultrasonic probe including a transducer including the piezoelectric element.

Through use of the ultrasonic probe of the present invention, there can be provided an ultrasonic diagnostic system including a receiving unit for receiving a signal output from the ultrasonic probe, which has driving efficiency comparable to or higher than that in the case of using a piezoelectric element containing lead.

The piezoelectric material of the present invention can be used in devices, such as an ultrasonic vibrator, a piezoelectric actuator, a piezoelectric sensor, and a ferroelectric memory, in addition to a liquid discharge head and a motor.

EXAMPLES

The present invention is hereinafter described more specifically by way of Examples. However, the present invention is not limited to the following Examples.

The piezoelectric ceramics of the present invention was produced.

Example 1

As raw material powders, barium titanate ($BaTiO_3$, Ba/Ti=0.9985) having an average grain size of 100 nm, calcium titanate ($CaTiO_3$, Ca/Ti=0.9978), calcium zirconate ($CaZrO_3$, Ca/Zr=0.999), trimanganese tetraoxide ($Mn_3O_4$), bismuth oxide ($Bi_2O_3$), tungsten oxide ($WO_3$), and barium carbonate for adjusting the ratio "a" of the sum of the numbers of moles of Ba and Ca with respect to the sum of the numbers of moles of Ti and Zr were used. Those raw material powders were weighed so as to obtain a ratio of the composition formula $(Ba_{0.86},Ca_{0.14})_{0.9994}(Ti_{0.93},Zr_{0.07})O_3$ containing titanium and barium as main components. Mn serving as a first sub-component, Bi serving as a second sub-component, and W serving as a third sub-component were added to 100 parts by mass of the metal oxide so that the content of Mn became 0.160 part by mass in terms of a metal, the content of Bi became 0.190 part by mass in terms of a metal, and the content of W became 0.312 part by mass in terms of a metal so as to have a content ratio in terms of a metal shown in Table 1. The resultant was mixed by dry mixing for 24 hours through use of a ball mill. In order to granulate the obtained mixed powder, 3 parts by mass of a PVA binder based on the mixed powder was caused to adhere to the surface of the mixed powder through use of a spray dryer device.

Next, the obtained granulated powder was filled in a mold, and a molding pressure of 200 MPa was applied thereto using a press molding machine to produce a disc-shaped molded body. The molded body may be further pressurized using a cold isostatic pressing molding machine.

The obtained molded body was placed in an electric furnace, kept at a maximum temperature of from 1,300° C. to 1,400° C. for 4 hours, and sintered in an air atmosphere over a total of 24 hours to provide a sintered body formed of the piezoelectric material of the present invention.

Then, the average equivalent circle diameter and the relative density of crystal grains forming the obtained sintered body were evaluated. As a result, the average equivalent circle diameter was 8.5 μm, and the relative density was 95% or more. A polarizing microscope was mainly used for observing the crystal grains. A scanning electron microscope (SEM) was used for identifying the grain sizes of small crystal grains. The average equivalent circle diameter was calculated from the observation results. In addition, the relative density was evaluated through use of the theoretical density calculated from the lattice constant obtained from X-ray diffraction and the weighed composition, and the measured density by the Archimedes method.

Next, the composition of the sintered body obtained by the ICP emission spectrometry was evaluated. As a result, the composition of Ba, Ca, Ti, Zr, Mn, Bi, and W after the sintering was matched with the weighed composition in all piezoelectric materials.

Next, the obtained sintered body was polished to a thickness of 0.5 mm, and the crystal structure was analyzed by X-ray diffraction. As a result, only the peak corresponding to the perovskite structure was observed.

($d_{31}$ Evaluation Element)

As a $d_{31}$ evaluation element, both surfaces of a sintered piezoelectric material were polished so that the piezoelectric material had a thickness of 0.5 mm, and gold electrodes each having a thickness of 400 nm were formed on both the front and rear surfaces of the piezoelectric material, which was subjected to annealing treatment under the condition of 900° C. in the atmosphere in an electric furnace, by a DC sputtering method. Titanium was formed into a film having a thickness of 30 nm as a contact layer between each of the electrodes and the piezoelectric material. The piezoelectric material with the electrodes was cut through use of a dicer to produce a strip-shaped piezoelectric element having a size of 10 mm×2.5 mm×0.5 mm. The surface of a hot plate was set to from 60° C. to 100° C., and an electric field of 1 kV/mm was applied between the electrodes of the obtained piezoelectric element on the hot plate for 30 minutes. Thus, polarization treatment was performed.

(d$_{33}$ Evaluation Element)

As a d$_{33}$ evaluation element, both the front and rear surfaces of a sintered piezoelectric material were polished, and the piezoelectric material was cut through use of a dicer to produce a plate-shaped piezoelectric material having a size of 5.0 mm×12.0 mm×0.90 mm. Then, a gold electrode was formed on a side surface of the plate-shaped piezoelectric material by forming gold into a film having a thickness of 400 nm by a DC sputtering method, and polishing and removing the gold film formed on the surface. Titanium was formed into a film having a thickness of 30 nm as a contact layer between each of the electrodes and the piezoelectric material. The plate-shaped piezoelectric material with the electrodes was cut again through use of a dicer to produce a prismatic piezoelectric element having a size of 0.80 mm×0.80 mm×5.0 mm. An electric field of 1 kV/mm was applied between the electrodes of the obtained piezoelectric element in oil set to from 80° C. to 100° C. for 30 minutes. Thus, polarization treatment was performed.

(Evaluation of Piezoelectric Characteristics)

In the following, as static characteristics of each of the piezoelectric elements including the piezoelectric materials of the present invention and the piezoelectric materials corresponding to Comparative Examples, the piezoelectric constant d$_{31}$ and the piezoelectric constant d$_{33}$ of the piezoelectric element subjected to the polarization treatment were evaluated by a resonance-antiresonance method. The phase transition temperatures T$_{to}$ and T$_C$ were calculated by measuring an electrostatic capacitance with an impedance analyzer (4194A manufactured by Agilent Technologies) while changing the temperature of each sample. At the same time, the temperature dependence of a dielectric loss tangent was also measured with the impedance analyzer. The temperature of the sample was temporarily cooled from room temperature to −100° C. and then heated to 150° C. The T$_{to}$, which was a temperature at which a crystal system was changed from a tetragonal crystal to an orthorhombic crystal, was defined as a temperature at which a value obtained by measuring a dielectric constant while cooling the sample and differentiating the dielectric constant with the sample temperature was maximized. The T$_C$, which was a temperature at which the dielectric constant became maximum in the vicinity of a phase transition temperature between a ferroelectric phase (tetragonal phase) and a paraelectric phase (cubic phase), was defined as a temperature at which a value obtained by measuring a dielectric constant while heating the sample became maximum.

In each of Examples 2 to 31 and Comparative Examples 1 to 22, a piezoelectric ceramics was produced by the same formulation as in Example 1 with the material composition shown in Table 1 and evaluated in the same manner.

TABLE 1

| | Main component | | | | | First sub-component Mn | Second sub-component Bi | Third sub-component W | Average grain |
|---|---|---|---|---|---|---|---|---|---|
| | Ba 1-x | Ca x | Ti 1-y | Zr y | a | Part(s) by mass | Part(s) by mass | Part(s) by mass | diameter μm |
| Example 1 | 0.860 | 0.140 | 0.930 | 0.070 | 0.9994 | 0.160 | 0.190 | 0.312 | 8.5 |
| Example 2 | 0.860 | 0.140 | 0.930 | 0.070 | 0.9994 | 0.160 | 0.190 | 0.209 | 6.2 |
| Example 3 | 0.860 | 0.140 | 0.930 | 0.070 | 0.9994 | 0.160 | 0.190 | 0.104 | 5.3 |
| Example 4 | 0.860 | 0.140 | 0.930 | 0.070 | 0.9994 | 0.160 | 0.190 | 0.380 | 9.7 |
| Example 5 | 0.860 | 0.140 | 0.930 | 0.070 | 0.9994 | 0.240 | 0.190 | 0.312 | 7.8 |
| Example 6 | 0.860 | 0.140 | 0.930 | 0.070 | 0.9994 | 0.160 | 0.050 | 0.312 | 8.6 |
| Example 7 | 0.860 | 0.140 | 0.930 | 0.070 | 0.9994 | 0.160 | 0.100 | 0.312 | 8.2 |
| Example 8 | 0.860 | 0.140 | 0.930 | 0.070 | 0.992 | 0.160 | 0.190 | 0.312 | 9.7 |
| Example 9 | 0.860 | 0.140 | 0.930 | 0.070 | 0.9994 | 0.060 | 0.190 | 0.312 | 7.8 |
| Example 10 | 0.860 | 0.140 | 0.930 | 0.070 | 0.9994 | 0.300 | 0.190 | 0.312 | 8.2 |
| Example 11 | 0.860 | 0.140 | 0.940 | 0.060 | 0.9994 | 0.160 | 0.190 | 0.312 | 8.2 |
| Example 12 | 0.860 | 0.140 | 0.940 | 0.060 | 0.9994 | 0.160 | 0.190 | 0.104 | 6.4 |
| Example 13 | 0.860 | 0.140 | 0.940 | 0.060 | 0.9994 | 0.240 | 0.190 | 0.312 | 7.7 |
| Example 14 | 0.860 | 0.140 | 0.915 | 0.085 | 0.9994 | 0.160 | 0.190 | 0.312 | 8.4 |
| Example 15 | 0.860 | 0.140 | 0.915 | 0.085 | 0.9994 | 0.160 | 0.190 | 0.209 | 7.1 |
| Example 16 | 0.860 | 0.140 | 0.915 | 0.085 | 0.9994 | 0.160 | 0.100 | 0.312 | 8.1 |
| Example 17 | 0.860 | 0.140 | 0.915 | 0.085 | 0.9994 | 0.160 | 0.240 | 0.312 | 7.4 |
| Example 18 | 0.890 | 0.110 | 0.975 | 0.025 | 0.9994 | 0.160 | 0.190 | 0.312 | 8.6 |
| Example 19 | 0.890 | 0.110 | 0.975 | 0.025 | 0.9994 | 0.160 | 0.190 | 0.209 | 7.3 |
| Example 20 | 0.890 | 0.110 | 0.975 | 0.025 | 0.9994 | 0.100 | 0.190 | 0.312 | 8.9 |
| Example 21 | 0.890 | 0.110 | 0.930 | 0.070 | 0.9994 | 0.160 | 0.190 | 0.312 | 7.6 |
| Example 22 | 0.890 | 0.110 | 0.930 | 0.070 | 0.9994 | 0.160 | 0.190 | 0.104 | 5.9 |
| Example 23 | 0.915 | 0.085 | 0.950 | 0.050 | 0.9994 | 0.160 | 0.190 | 0.312 | 8.4 |
| Example 24 | 0.915 | 0.085 | 0.950 | 0.050 | 0.9994 | 0.160 | 0.190 | 0.209 | 7.2 |
| Comparative Example 1 | 0.860 | 0.140 | 0.930 | 0.070 | 0.9994 | 0.160 | 0.190 | 0.000 | 3.2 |
| Comparative Example 2 | 0.860 | 0.140 | 0.930 | 0.070 | 0.9994 | 0.160 | 0.190 | 0.052 | 5.1 |
| Comparative Example 3 | 0.860 | 0.140 | 0.930 | 0.070 | 0.9994 | 0.160 | 0.190 | 0.400 | 15.0 |
| Comparative Example 4 | 0.920 | 0.080 | 0.950 | 0.050 | 0.9994 | 0.160 | 0.190 | 0.312 | 2.1 |

TABLE 1-continued

| | Main component | | | | | First sub-component Mn | Second sub-component Bi | Third sub-component W | Average grain |
| | Ba 1-x | Ca x | Ti 1-y | Zr y | a | Part(s) by mass | Part(s) by mass | Part(s) by mass | diameter μm |
|---|---|---|---|---|---|---|---|---|---|
| Comparative Example 5 | 0.685 | 0.315 | 0.950 | 0.050 | 0.9994 | 0.160 | 0.190 | 0.312 | 6.2 |
| Comparative Example 6 | 0.685 | 0.315 | 0.950 | 0.050 | 0.9994 | 0.160 | 0.190 | 0.000 | 2.1 |
| Comparative Example 7 | 0.685 | 0.315 | 0.930 | 0.070 | 0.9994 | 0.160 | 0.190 | 0.052 | 4.4 |
| Comparative Example 8 | 0.830 | 0.170 | 0.910 | 0.090 | 0.9994 | 0.160 | 0.190 | 0.312 | 6.5 |
| Comparative Example 9 | 0.830 | 0.170 | 0.910 | 0.090 | 0.9994 | 0.160 | 0.190 | 0.000 | 2.4 |
| Comparative Example 10 | 0.830 | 0.170 | 0.910 | 0.090 | 0.9994 | 0.160 | 0.190 | 0.052 | 5.6 |
| Comparative Example 11 | 0.890 | 0.110 | 0.980 | 0.020 | 0.9994 | 0.160 | 0.190 | 0.312 | 8.4 |
| Comparative Example 12 | 0.890 | 0.110 | 0.980 | 0.020 | 0.9994 | 0.160 | 0.190 | 0.000 | 3.1 |
| Comparative Example 13 | 0.890 | 0.110 | 0.930 | 0.070 | 0.9994 | 0.160 | 0.190 | 0.052 | 4.7 |
| Comparative Example 14 | 1.000 | 0.000 | 1.000 | 0.000 | 0.9994 | 0.160 | 0.190 | 0.312 | 8.3 |
| Comparative Example 15 | 1.000 | 0.000 | 1.000 | 0.000 | 0.9994 | 0.160 | 0.190 | 0.000 | 2.8 |
| Comparative Example 16 | 0.860 | 0.140 | 0.930 | 0.070 | 0.9994 | 0.030 | 0.190 | 0.000 | 3.4 |
| Comparative Example 17 | 0.860 | 0.140 | 0.930 | 0.070 | 0.9994 | 0.160 | 0.040 | 0.312 | 8.6 |
| Comparative Example 18 | 0.700 | 0.300 | 0.930 | 0.070 | 0.9994 | 0.160 | 0.190 | 0.312 | 7.6 |
| Comparative Example 19 | 0.700 | 0.300 | 0.930 | 0.070 | 0.9994 | 0.160 | 0.190 | 0.104 | 5.3 |
| Comparative Example 20 | 0.700 | 0.300 | 0.930 | 0.070 | 0.992 | 0.160 | 0.190 | 0.312 | 10.6 |
| Comparative Example 21 | 0.700 | 0.300 | 0.930 | 0.070 | 1.002 | 0.160 | 0.190 | 0.312 | 6.1 |
| Comparative Example 22 | 0.700 | 0.300 | 0.975 | 0.025 | 0.9994 | 0.160 | 0.190 | 0.052 | 4.4 |
| Comparative Example 23 | 0.700 | 0.300 | 0.975 | 0.025 | 0.9994 | 0.160 | 0.190 | 0.312 | 7.4 |
| Comparative Example 24 | 0.700 | 0.300 | 0.975 | 0.025 | 0.9994 | 0.160 | 0.190 | 0.209 | 6.3 |
| Comparative Example 25 | 0.700 | 0.300 | 0.975 | 0.025 | 0.9994 | 0.160 | 0.100 | 0.312 | 7.6 |
| Comparative Example 26 | 0.700 | 0.300 | 0.975 | 0.025 | 0.9994 | 0.160 | 0.240 | 0.312 | 8.1 |
| Comparative Example 27 | 0.860 | 0.140 | 0.930 | 0.070 | 0.9850 | 0.160 | 0.190 | 0.312 | 50.0 |
| Comparative Example 28 | 0.700 | 0.300 | 0.930 | 0.070 | 1.0400 | 0.160 | 0.190 | 0.312 | 1.6 |
| Comparative Example 29 | 0.860 | 0.140 | 0.915 | 0.085 | 0.9994 | 0.160 | 0.260 | 0.312 | 7.4 |

In Table 2, the piezoelectric constant $d_{31}$ and the piezoelectric constant $d_{33}$ at room temperature, the electromechanical coupling coefficient $k_{33}$, the change rate of the piezoelectric constant $d_{33}$, the dielectric loss tangent $\tan \delta$, the Curie temperature $T_C$, and the phase transition temperature $T_{to}$ of Examples and Comparative Examples shown in Table 1 are summarized.

TABLE 2

| | $d_{31}$ pm/V | $d_{33}$ pm/V | $k_{33}$ % | Change rate of $d_{33}$ — | Dielectric loss tangent $\tan\delta$ — | Curie temperature $T_C$ ° C. | Phase transition temperature $T_{to}$ ° C. |
|---|---|---|---|---|---|---|---|
| Example 1 | 110 | 270 | 59.9 | 0.203 | 0.004 | 90 | −24 |
| Example 2 | 103 | 253 | 59.2 | 0.221 | 0.003 | 100 | −24 |
| Example 3 | 103 | 253 | 59.2 | 0.225 | 0.002 | 101 | −23 |
| Example 4 | 105 | 258 | 58.1 | 0.204 | 0.004 | 87 | −25 |

TABLE 2-continued

| | $d_{31}$ pm/V | $d_{33}$ pm/V | $k_{33}$ % | Change rate of $d_{33}$ — | Dielectric loss tangent tanδ — | Curie temperature $T_C$ ° C. | Phase transition temperature $T_{to}$ ° C. |
|---|---|---|---|---|---|---|---|
| Example 5 | 103 | 253 | 57 | 0.21 | 0.004 | 91 | −25 |
| Example 6 | 111 | 272 | 60.2 | 0.285 | 0.004 | 90 | −2 |
| Example 7 | 109 | 268 | 60.3 | 0.271 | 0.004 | 91 | −13 |
| Example 8 | 101 | 248 | 57.1 | 0.209 | 0.003 | 92 | −27 |
| Example 9 | 111 | 272 | 60.3 | 0.204 | 0.009 | 90 | −25 |
| Example 10 | 107 | 263 | 57.3 | 0.211 | 0.002 | 91 | −28 |
| Example 11 | 108 | 265 | 58.1 | 0.213 | 0.004 | 95 | −31 |
| Example 12 | 106 | 260 | 57.3 | 0.222 | 0.003 | 99 | −33 |
| Example 13 | 105 | 258 | 56.4 | 0.218 | 0.002 | 97 | −33 |
| Example 14 | 116 | 285 | 60.8 | 0.201 | 0.004 | 85 | −15 |
| Example 15 | 110 | 270 | 60.1 | 0.216 | 0.003 | 95 | −18 |
| Example 16 | 116 | 285 | 60.8 | 0.221 | 0.004 | 85 | −7 |
| Example 17 | 113 | 277 | 60.4 | 0.216 | 0.002 | 86 | −22 |
| Example 18 | 109 | 268 | 59.1 | 0.22 | 0.003 | 100 | −28 |
| Example 19 | 105 | 258 | 58.3 | 0.201 | 0.003 | 110 | −29 |
| Example 20 | 108 | 265 | 58.9 | 0.219 | 0.003 | 99 | −29 |
| Example 21 | 113 | 277 | 58.3 | 0.202 | 0.004 | 90 | −18 |
| Example 22 | 106 | 260 | 56.1 | 0.217 | 0.003 | 100 | −24 |
| Example 23 | 109 | 268 | 58.6 | 0.218 | 0.005 | 96 | −25 |
| Example 24 | 108 | 265 | 57.8 | 0.22 | 0.005 | 98 | −26 |
| Comparative Example 1 | 96 | 236 | 57.1 | 0.332 | 0.002 | 106 | −21 |
| Comparative Example 2 | 93 | 228 | 56.6 | 0.219 | 0.002 | 102 | −23 |
| Comparative Example 3 | 101 | 248 | 53.2 | 0.211 | 0.007 | 85 | −22 |
| Comparative Example 4 | 92 | 226 | 54.3 | 0.312 | 0.005 | 90 | −33 |
| Comparative Example 5 | 88 | 216 | 51.8 | 0.271 | 0.003 | 99 | −51 |
| Comparative Example 6 | 76 | 187 | 48.3 | 0.303 | 0.003 | 111 | −53 |
| Comparative Example 7 | 89 | 218 | 52.4 | 0.278 | 0.002 | 102 | −49 |
| Comparative Example 8 | 118 | 290 | 58.6 | 0.364 | 0.016 | 84 | 2 |
| Comparative Example 9 | 98 | 241 | 53.4 | 0.316 | 0.016 | 98 | 1 |
| Comparative Example 10 | 109 | 268 | 58.2 | 0.33 | 0.003 | 97 | −20 |
| Comparative Example 11 | 85 | 209 | 48.4 | 0.226 | 0.012 | 111 | −33 |
| Comparative Example 12 | 79 | 194 | 44.1 | 0.346 | 0.012 | 122 | −34 |
| Comparative Example 13 | 105 | 258 | 55.4 | 0.328 | 0.002 | 103 | −26 |
| Comparative Example 14 | 76 | 187 | 43.4 | 0.316 | 0.015 | 113 | −13 |
| Comparative Example 15 | 68 | 167 | 42.1 | 0.323 | 0.015 | 121 | −14 |
| Comparative Example 16 | 98 | 241 | 56.4 | 0.311 | 0.018 | 101 | −26 |
| Comparative Example 17 | 114 | 280 | 61.1 | 0.372 | 0.004 | 90 | 7 |
| Comparative Example 18 | 92 | 226 | 54.3 | 0.198 | 0.004 | 92 | −45 |
| Comparative Example 19 | 90 | 221 | 53.1 | 0.208 | 0.003 | 99 | −47 |
| Comparative Example 20 | 91 | 223 | 54 | 0.235 | 0.002 | 94 | −46 |
| Comparative Example 21 | 91 | 223 | 54.2 | 0.186 | 0.005 | 92 | −43 |
| Comparative Example 22 | 83 | 204 | 49.1 | 0.308 | 0.002 | 110 | −53 |
| Comparative Example 23 | 86 | 211 | 50.6 | 0.216 | 0.003 | 97 | −48 |
| Comparative Example 24 | 84 | 206 | 49.8 | 0.226 | 0.003 | 105 | −52 |
| Comparative Example 25 | 87 | 214 | 51.2 | 0.224 | 0.004 | 96 | −33 |
| Comparative Example 26 | 86 | 211 | 50.3 | 0.226 | 0.001 | 99 | −51 |
| Comparative Example 27 | 86 | 211 | 53.2 | 0.228 | 0.003 | 90 | −27 |
| Comparative Example 28 | 88 | 216 | 50.1 | 0.211 | 0.015 | 90 | −27 |

TABLE 2-continued

| | $d_{31}$ pm/V | $d_{33}$ pm/V | $k_{33}$ % | Change rate of $d_{33}$ — | Dielectric loss tangent tanδ — | Curie temperature $T_C$ ° C. | Phase transition temperature $T_{to}$ ° C. |
|---|---|---|---|---|---|---|---|
| Comparative Example 29 | 83 | 204 | 48.8 | 0.201 | 0.003 | 92 | −58 |

Figure 18:
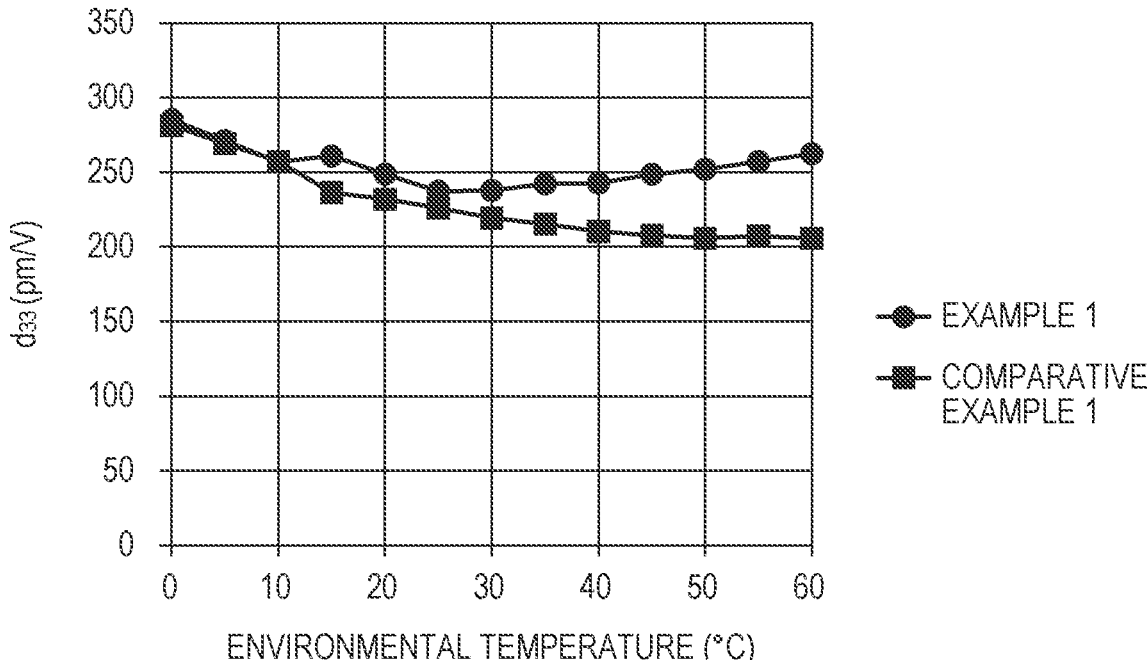
FIG. 18 is a graph for showing changes in piezoelectric constant $d_{33}$ of the piezoelectric material of the present invention with respect to an environmental temperature.

In FIG. 18, there is shown the temperature dependence of the piezoelectric constant $d_{33}$ at an environmental temperature of from 0° C. to 60° C. of Example 1 and Comparative Example 1. The change rate of $d_{33}$ was calculated from the graph of FIG. 18 through use of the expression (3). Comparative Example 1 had the same composition as that of Example 1 except that W was not contained, but the change rate of $d_{33}$ was 0.332, which was larger than the change rate of $d_{33}$ of 0.203 of Example 1 in which the content of W was 0.312. In addition, in Comparative Example 2 in which the content of W was 0.052, the change rate of $d_{33}$ was small, but the $d_{33}$ was as low as 228 pm/V.

Figure 17:
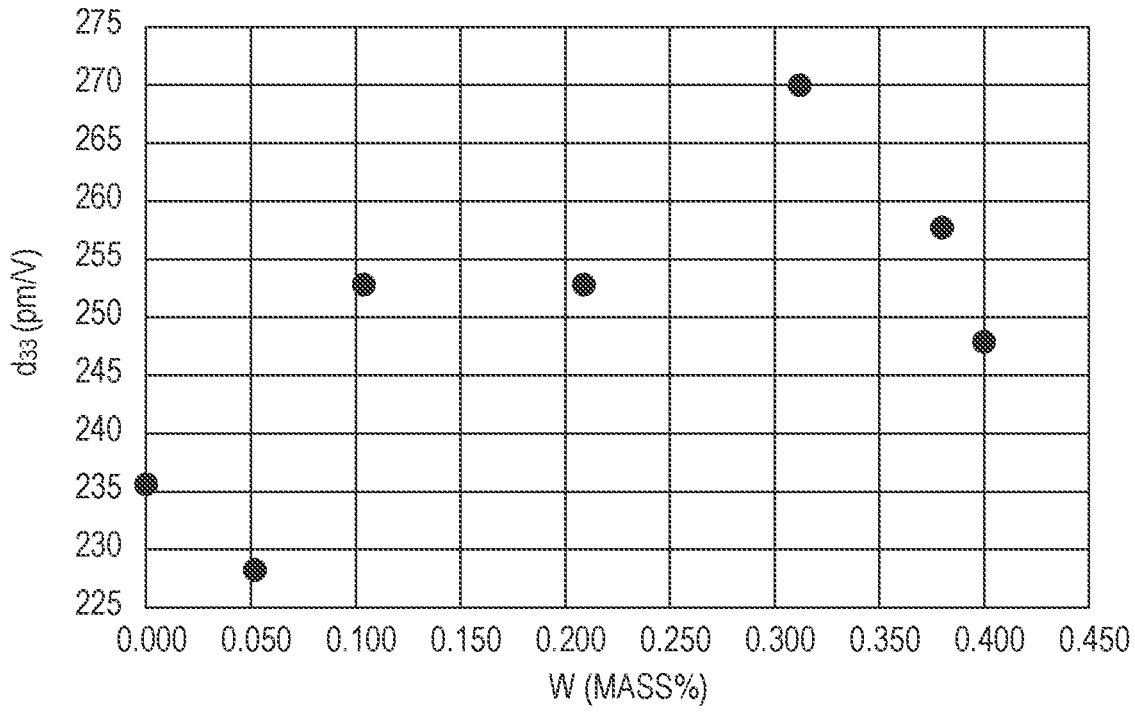
FIG. 17 is a graph for showing W addition amount dependence of a piezoelectric constant $d_{33}$ of a piezoelectric material of the present invention.

In FIG. 17, there are shown changes in piezoelectric constant $d_{33}$ with respect to the content of W. Examples 2 to 4 and Comparative Examples 1 to 3 each have the same composition as that of Example 1 except for the content of W. The following is found from FIG. 17. It was not the case that the piezoelectric constant $d_{33}$ was increased when W was contained even in a small amount. When W was contained to a certain degree, specifically, when the content was 0.100 or more, the effect of improving the piezoelectric constant $d_{33}$ was exhibited, and the piezoelectric constant $d_{33}$ was 240 pm/V or more, which was expected to satisfy the piezoelectric device performance. In addition, also regarding the upper limit, the $d_{33}$ of Comparative Example 3 having a content of W of 0.400 was as low as 248 pm/V while the $d_{33}$ of Example 4 having a content of W of 0.380 was 258 pm/V. Although the piezoelectric material of Comparative Example 3 satisfied 240 pm/V, the average grain size thereof was as large as 15 μm, and for example, chipping was observed at the time of cutting processing. Thus, the piezoelectric material of Comparative Example 3 had poor processability. Accordingly, due to the influence of chipping or the like, the piezoelectric material having the composition of Comparative Example 3 had an effective piezoelectric constant $d_{33}$ that was lower by 5% or more than that obtained from the sample of Comparative Example 3.

In Comparative Example 4, the Ca amount "x" was as small as 0.080. Because of this, the $T_C$ was 106° C., and the $T_{to}$ was −33° C. Accordingly, the $d_{33}$ was lower by 42 pm/V than that of Example 23 in which the Ca amount "x" was 0.085 and the Ti, Zr, Mn, Bi, and W amounts were the same as those in Comparative Example 4.

In Comparative Example 5, the Ca amount "x" was as large as 0.315. When X-ray diffraction measurement was performed, a CaTiO$_3$ phase was detected. The change rate of $d_{33}$ was 0.271, which was less than 0.3, and the $d_{33}$ was stable with respect to the temperature. However, the piezoelectric constant $d_{33}$ at room temperature was 216 pm/V, which was 240 pm/V or less.

In Comparative Example 8, the Zr amount "y" was as large as 0.09. Because of this, the Curie temperature $T_C$ was 84° C., which was less than 90° C., and also the $T_{to}$ was 2° C., which was more than 0° C. Thus, the phase transition temperatures fell within a practical temperature range. In this case, the change rate of $d_{33}$ was as large as 0.364, and the dielectric loss tangent tan δ was also as large as 0.16.

In Comparative Example 11, the Zr amount "y" was as small as 0.020. The piezoelectric constant $d_{33}$ was lower by 68 pm/V than that of Example 21 (y=0.070) in which the Ca amount was the same.

In Comparative Example 27, the "a" was as small as 0.985, and hence abnormal grain growth was observed. The material had a grain size as large as 50 μm and hence had poor processability, and the piezoelectric constant $d_{33}$ was 211 pm/V, which was 240 pm/V or less.

In Comparative Example 28, the "a" was as large as 1.004, and hence the growth of crystal grains was poor, and the grain size was as small as 1.6 μm. Thus, the piezoelectric constant $d_{33}$ was 216 pm/V, which was 240 pm/V or less, and the dielectric loss tangent tan δ was as large as 0.015.

In Comparative Example 17, the Bi amount was as small as 0.04. Because of this, the $T_{to}$ was 7° C., which was more than the practical temperature lower limit of 0° C. The change rate of $d_{33}$ in this case was as large as 0.372.

In Comparative Example 29, the Bi amount was as large as 0.26. Because of this, although the change rate of $d_{33}$ was as small as 0.201, the piezoelectric constant $d_{33}$ at room temperature was 204 pm/V, which was 240 pm/V or less.

Example 32

Barium titanate (BaTiO$_3$), calcium titanate (CaTiO$_3$), calcium zirconate (CaZrO$_3$), trimanganese tetraoxide (Mn$_3$O$_4$), tungsten oxide (WO$_3$), bismuth oxide (Bi$_2$O$_3$), and a glass aid containing Si and B (containing SiO$_2$ in an amount of from 30 mass % to 50 mass % and B$_2$O$_3$ in an amount of 21.1 mass %) were weighed so as to have the composition of Example 32 in Table 1. The weighed raw material powders were mixed, and mixed overnight in a ball mill to obtain mixed powder.

PVB was added to the obtained mixed powder, the materials were mixed, and then the mixture was formed into a sheet by a doctor blade method to provide a green sheet having a thickness of 50 μm.

A conductive paste for an internal electrode was printed on the green sheet. As the conductive paste, a Ag 60%-Pd 40% alloy paste was used. Nine of the green sheets coated with the conductive paste were stacked, and the multilayered body was fired under the condition of 1,200° C. for 5 hours to provide a sintered body. After the sintered body was cut to a size of 10 mm×2.5 mm, the side surface thereof was polished, and a pair of external electrodes (first electrode and second electrode) for short-circuiting the internal electrodes alternately was formed by Au sputtering to produce a multilayered piezoelectric element as illustrated in FIG. 2B.

When the internal electrodes of the obtained multilayered piezoelectric element were observed, Ag—Pd, which was an electrode material, was formed alternately with the piezoelectric material.

Prior to the evaluation of piezoelectricity, the sample was subjected to polarization treatment. Specifically, the sample was heated to 100° C. in an oil bath. Then, a voltage of 1 kV/mm was applied between the first electrode and the second electrode for 30 minutes, and the sample was cooled to room temperature while the voltage was applied.

When the piezoelectricity of the obtained multilayered piezoelectric element was evaluated, the multilayered piezoelectric element had a sufficient insulating property, and satisfactory piezoelectric characteristics comparable to those of the piezoelectric material of Example 1 were able to be obtained.

Example 33

Mixed powder was prepared by the same procedure as in Example 32. The obtained mixed powder was calcined in the atmosphere at 1,000° C. for 3 hours while being rotated in a rotary kiln to obtain calcined powder. The obtained calcined powder was crushed through use of a ball mill. PVB was added to the obtained crushed powder, the materials were mixed, and then the mixture was formed into a sheet by a doctor blade method to obtain a green sheet having a thickness of 50 μm. A conductive paste for an internal electrode was printed on the green sheet. A Ni paste was used as the conductive paste.

Nine of the green sheets coated with the conductive paste were stacked, and the multilayered body was subjected to thermocompression bonding.

The multilayered body subjected to thermocompression bonding was fired in a tube furnace. The firing was performed in the atmosphere up to 300° C., and after binder removal, the atmosphere was switched to a reducing atmosphere ($H_2:N_2=2:98$, oxygen concentration: $2\times10^{-6}$ Pa) and maintained at 1,200° C. for 5 hours. In the temperature decrease process, the temperature was cooled to room temperature by switching the oxygen concentration to 30 Pa from a temperature of 1,000° C. or less.

After the sintered body thus obtained was cut to a size of 10 mm×2.5 mm, the side surface thereof was polished, and a pair of external electrodes (first electrode and second electrode) for short-circuiting the internal electrodes alternately was formed by Au sputtering to produce a multilayered piezoelectric element as illustrated in FIG. 2B.

When the internal electrodes of the obtained multilayered piezoelectric element were observed, Ni, which was an electrode material, was formed alternately with the piezoelectric material layer. The obtained multilayered piezoelectric element was subjected to polarization treatment through application of an electric field of 1 kV/mm for 30 minutes in an oil bath maintained at 100° C. When the piezoelectric characteristics of the obtained multilayered piezoelectric element were evaluated, the multilayered piezoelectric element had a sufficient insulating property, and satisfactory piezoelectric characteristics comparable to those of the piezoelectric element of Example 32 were able to be obtained.

Example 34

The liquid discharge head illustrated in FIG. 3A and FIG. 3B was produced through use of the piezoelectric element of Example 1. The discharge of ink in accordance with an input electric signal was recognized.

Example 35

The liquid discharge device illustrated in FIG. 4 was produced through use of the liquid discharge head of Example 34. The discharge of ink onto a recording medium in accordance with an input electric signal was recognized.

Example 36

The ultrasonic motor illustrated in FIG. 6A was produced through use of the piezoelectric element of Example 1. The rotation of the motor in accordance with the application of an AC voltage was recognized.

Example 37

The optical apparatus illustrated in FIG. 7A and FIG. 7B was produced through use of the ultrasonic motor of Example 36. An autofocus operation in accordance with the application of an AC voltage was recognized.

Example 38

The dust removing device illustrated in FIG. 9A and FIG. 9B was produced through use of the piezoelectric element of Example 1. When plastic beads were sprayed and an AC voltage was applied, a satisfactory dust removing rate was recognized.

Example 39

The image pickup apparatus illustrated in FIG. 12 was produced through use of the dust removing device of Example 38. When the apparatus was operated, dust on the surface of an image pickup unit was satisfactorily removed, and an image without dust defects was obtained.

Example 40

The electronic apparatus illustrated in FIG. 14 was produced through use of the piezoelectric element of Example 1. In the produced electronic apparatus, a speaker operation in accordance with the application of an AC voltage was recognized.

Example 41

The ultrasonic probe illustrated in FIG. 15 was produced through use of the piezoelectric element of Example 1. In the produced ultrasonic probe, ultrasonic waves were transmitted by the application of an AC voltage, and a reception signal caused by reflection from the inside of an object was recognized.

Example 42

The ultrasonic diagnostic system illustrated in FIG. 16 was produced through use of the ultrasonic probe of Example 41. When the produced ultrasonic diagnostic system was operated, an image of the inside of an object was clearly output.

Example 43

The liquid discharge head illustrated in FIG. 3A and FIG. 3B was produced through use of the multilayered piezoelectric element of Example 32. The discharge of ink in accordance with an input electric signal was recognized.

Example 44

The liquid discharge device illustrated in FIG. 4 was produced through use of the liquid discharge head of Example 43. The discharge of ink onto a recording medium in accordance with an input electric signal was recognized.

Example 45

The ultrasonic motor illustrated in FIG. 6B was produced through use of the multilayered piezoelectric element of Example 32. The rotation of the motor in accordance with the application of an AC voltage was recognized.

Example 46

The optical apparatus illustrated in FIG. 7A and FIG. 7B was produced through use of the ultrasonic motor of Example 45. An autofocus operation in accordance with the application of an AC voltage was recognized.

Example 47

The dust removing device illustrated in FIG. 9A and FIG. 9B was produced through use of the multilayered piezoelectric element of Example 32. When plastic beads were sprayed and an AC voltage was applied, a satisfactory dust removing rate was recognized.

Example 48

The image pickup apparatus illustrated in FIG. 12 was produced through use of the dust removing device of Example 47. When the apparatus was operated, dust on the surface of an image pickup unit was satisfactorily removed, and an image without dust defects was obtained.

Example 49

The electronic apparatus illustrated in FIG. 14 was produced through use of the multilayered piezoelectric element of Example 32. A speaker operation in accordance with the application of an AC voltage was recognized.

The piezoelectric material of the present invention exhibits satisfactory piezoelectricity in a wide environmental temperature region. In addition, the piezoelectric material is free of lead, and hence has a small burden on the environment. Accordingly, the piezoelectric material of the present invention can be used without problems even in a device that uses a large amount of a piezoelectric material, such as a liquid discharge head, an ultrasonic motor, a dust removing device, and an ultrasonic diagnostic system.

According to the present invention, the piezoelectric material which is free of lead, has small temperature dependence of a piezoelectric constant within an operating temperature range, and has a satisfactory piezoelectric constant can be provided. The piezoelectric material of the present invention does not use lead, and hence has a small burden on the environment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-039641, filed Mar. 11, 2021, which is hereby incorporated by reference herein in its entirety.

What is claimed is:

1. A piezoelectric material comprising:
an oxide having a perovskite-type structure containing Ba, Ca, Ti, and Zr; Mn; Bi; and W,
wherein "x", which represents a molar ratio of the Ca with respect to a sum of the Ba and the Ca, satisfies 0.085≤x≤0.150,
wherein "y", which represents a molar ratio of the Zr with respect to a sum of the Ti and the Zr, satisfies 0.025≤y≤0.085,
wherein a ratio of the sum of the Ba and the Ca with respect to the sum of the Ti and the Zr is 0.986 to 1.02,
wherein, in terms of a metal with respect to 100 parts by mass of the oxide:
a content of the Mn is 0.040 part by mass to 0.360 part by mass;
a content of the Bi is 0.050 part by mass to 0.240 part by mass; and
a content of the W is 0.100 part by mass to 0.380 part by mass, and
wherein the piezoelectric material has an average equivalent circle diameter of a crystal of 2.0 μm to 12.0 μm.

2. The piezoelectric material according to claim 1, wherein the piezoelectric material is polarized.

3. The piezoelectric material according to claim 1, wherein the oxide is represented by formula (1):

$$(Ba_{1-x}Ca_x)_a(Ti_{1-y}Zr_y)O_3 \tag{1},$$

where "x", "y", and "a" satisfy 0.085≤x≤0.150, 0.025≤y≤0.085, and 0.986≤a≤1.02, respectively.

4. The piezoelectric material according to claim 1, wherein the piezoelectric material has a dielectric loss tangent at a frequency of 1 kHz of 0.010 or less.

5. A piezoelectric element comprising:
an electrode; and
a piezoelectric material portion,
wherein the piezoelectric material portion contains the piezoelectric material of claim 1.

6. The piezoelectric element according to claim 5, wherein the electrode and the piezoelectric material portion are stacked alternately.

7. The piezoelectric element according to claim 6, wherein the electrode contains Ag and Pd, and
wherein a mass ratio M1/M2 between a content mass M1 of the Ag and a content mass M2 of the Pd is 0.25≤M1/M2≤4.0.

8. The piezoelectric element according to claim 6, wherein the electrode contains at least any one kind selected from the group consisting of: Ni and Cu.

9. A liquid discharge head comprising:
a liquid chamber including a vibration unit including the piezoelectric element of claim 5; and
a discharge port communicating to the liquid chamber.

10. A liquid discharge device comprising:
an object-carrying unit; and
the liquid discharge head of claim 9.

11. A vibration actuator comprising:
a vibrating body including the piezoelectric element of claim 5; and
a contact body to be brought into contact with the vibrating body.

12. An optical apparatus comprising a drive unit including the vibration actuator of claim 11.

13. A vibration device comprising a vibrating body including a diaphragm including the piezoelectric element of claim 5.

14. A dust removing device comprising a vibration unit including the vibration device of claim 13.

15. An image pickup apparatus comprising:

the dust removing device of claim 14; and an image pickup element unit, wherein the diaphragm of the dust removing device is arranged on a light receiving plane side of the image pickup element unit.

16. A piezoelectric acoustic component comprising the piezoelectric element of claim 5.

17. An ultrasonic probe comprising a transducer including the piezoelectric element of claim 5.

18. An ultrasonic diagnostic system comprising:

the ultrasonic probe of claim 17; and a receiving unit configured to receive a signal output from the ultrasonic probe.

19. An electronic apparatus comprising:

a member; and the piezoelectric element of claim 5.

* * * * *